(12) United States Patent
Broka et al.

(10) Patent No.: US 7,049,325 B2
(45) Date of Patent: May 23, 2006

(54) QUINOLINE DERIVATIVES AS ANTI-INFLAMMATORY AGENTS

(75) Inventors: Chris Allen Broka, Foster City, CA (US); Woongki Kim, Cupertino, CA (US); David Bernard Smith, San Mateo, CA (US); Kevin L. McLaren, Carmel, IN (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 503 days.

(21) Appl. No.: 09/925,883

(22) Filed: Aug. 7, 2001

(65) Prior Publication Data

US 2002/0082276 A1    Jun. 27, 2002

Related U.S. Application Data

(60) Provisional application No. 60/224,196, filed on Aug. 9, 2000.

(51) Int. Cl.
C07D 215/16    (2006.01)
C07D 215/20    (2006.01)
A61K 31/47     (2006.01)

(52) U.S. Cl. ............... 514/312; 514/313; 514/314; 546/153; 546/159; 546/164

(58) Field of Classification Search ............... 546/165, 546/153, 159, 164; 514/312, 313, 314
See application file for complete search history.

(56) References Cited

U.S. PATENT DOCUMENTS

| | | | |
|---|---|---|---|
| 5,221,677 A | | 6/1993 | Crawley et al. |
| 5,594,143 A | * | 1/1997 | Kirk et al. ............ 546/157 |
| 5,962,531 A | | 10/1999 | Rotstein et al. |
| 6,069,151 A | | 5/2000 | Dyke et al. |
| 6,077,850 A | | 6/2000 | Carter et al. |
| 6,262,074 B1 | * | 7/2001 | Otten et al. ............ 514/314 |
| 6,479,436 B1 | * | 11/2002 | Otten et al. ............ 504/247 |

FOREIGN PATENT DOCUMENTS

| | | |
|---|---|---|
| EP | 0498722 A1 | 8/1992 |
| EP | 0498723 A1 | 8/1992 |
| WO | WO 95/11592 | 5/1995 |
| WO | WO 96/33717 A | 10/1996 |

OTHER PUBLICATIONS

Expert Opinion Pharmacother. (2003) 4(2):265-284, "Clinical Pharmacology of eloricoxib: a novel selective Cox-2 inhibitor", Patrignani et. al.*

Ca 139:345166, "Non-steroidal anti-inflammatory drugs and cyclooxygenase i Alzheimer's disease", Hoozemans et. al., Curren Drug Targets (2003), 4(6), 461-468.*
Anderson, et al., "The Role of Cyclooxygenase Inhibitors in Cancer Prevention," Current Pharmaceutical Design, 2002, pp. 1035-1062, vol. 8.
DeRuiter, et al., "Synthesis and Aldose Reductase Inhibitory Activity of Substituted 2-Oxoquinoline-1-acetic Acid Derivatives," J. Med. Chem., 1986, pp. 2024-2028, vol. 29.
Ding, et al., "Cyclooxygenases and Lipoxygenases as Potential Targets for Treatment of Pancreatic Cancer," Pancreatology, 2001, pp. 291-299, vol. 1.
Gassman; et al., "A General Method for the Synthesis of Isatins," J. Org. Chem., 1977 pp. 1344-1348, vol. 42:8.
Hewawasam, et al., "A General Method for the Synthesis of Isatins: Preparation of Regiospecifically Functionalized Isatins from Anilines," Tetrahedron Letters, 1994, pp. 7303-7306, vol. 35:40.
Kraynack, et al., "An Improved Procedure for the Regiospecific Synthesis of Electron Deficient 4- and 6-Substituted Isatins," Tetrahedron Letters, 1998, pp. 7679-7682, vol. 39.
Ozawa, et al., "Palladium-Catalyzed Double Carbonylation of Aryl Halides Affording α-Keto Amides, Applications to Synthesis of Isatin and Quinoline Derivatives," J. Org. Chem., 1986 pp. 415-417, vol. 51.

(Continued)

Primary Examiner—D. Margaret Seaman
(74) Attorney, Agent, or Firm—Grant D. Green

(57) ABSTRACT

This invention relates to compounds, which are generally anti-inflammatory and analgesic compounds, and which are represented by Formula I:

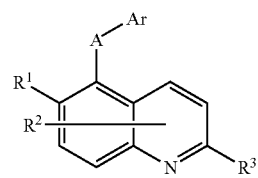

wherein A is a $CH_2$, CH(OH), C(O), C=$NOR^4$, $NR^5$, O, S, S(O), or $S(O)_2$, and the other substituents are as defined in the specification; or prodrugs, individual isomers, mixtures of isomers, and pharmaceutically acceptable salts thereof. The invention further relates to pharmaceutical compositions containing such compounds and methods for their use as therapeutic agents 33 Claims, No Drawings

OTHER PUBLICATIONS

Rahme, et al., "The Cyclooxygenase-2-Selective Inhibitors Rofecoxib and Celecoxib Prevent Colorectal Neoplasis Occurrence and Recurrence," Gastroenterology, 2003, pp. 404-412, vol. 125.

Sanchez-Alcaza, et al., "Cyclooxygenase (COX) inhibitors induce apoptosis in non-small cell lung cancer through cyclooxygenase independent pathways," Lung Cancer, 2003, pp. 33-44, vol. 40.

Singh-Ranger, et al., "Current concepts in cyclooxygenase inhibition in breast cancer," J. of Clinical Pharmacy and Therapeutics, 2002, pp. 321-327, vol. 27.

Steele, et al., "Mechanisms and applications of non-steroidal anti-inflammatory drugs in the chemoprevention of cancer," Mutation Research, 2003, pp. 137-144, vol. 523-524.

Morrison & Boyd, "Organic Chemistry", $3^{rd}$ Ed. (1973; Allyn and Bacon, Inc., Pub., Boston, MA) pp. 36-37.

* cited by examiner

US 7,049,325 B2

QUINOLINE DERIVATIVES AS ANTI-INFLAMMATORY AGENTS

CROSS REFERENCE TO RELATED APPLICATIONS

This Application claims benefit under Title 35 U.S.C. 119(e) of U.S. Provisional Aplication No. 60/224,196 filed Aug. 9, 2000; hereby incorporated as reference in its entirety.

BACKGROUND OF THE INVENTION

1. Field of the Invention

This invention relates to anti-inflammatory and analgesic compounds, especially to certain quinoline derivatives, pharmaceutical compositions containing them, methods for their use, and methods for preparing these compounds.

2. Background of the Invention

Non-steroidal, antiinflammatory drugs (NSAIDs), have a problem of causing serious side-effects such as gastrointestinal tract or nephro-toxicity. NSAIDs inhibit the activity of cyclooxygenase (COX), which is an enzyme involved in prostaglandin G/H synthesis, resulting in the inhibition of the biosynthesis of prostaglandins not only in inflammatory loci but also in stomach and kidney. It has been found that COX exists in two forms: COX-1 and COX-2, *Cell,* 83, 345, (1995).

COX-1 is expresed in normal cells and controls the function of stomach and kidney, while COX-2 is induced by mitogens or cytokines in inflammatory sites where inflammation and other immunoreactions occur, *J. Biol. Chem.,* 271, 33157(1996).

To avoid the toxicity of NSAIDs due to the inhibition of coexisting COX-1, selective inhibitors of COX-2 have been investigated. The selective COX-2 inhibitors have antiinflammatory action, pain-relieving action, and/or antipyretic action; with less side effects, such as bleeding in the gastrointestinal tract, COX-2 inhibitors may show anticancer activity, and lower the induction of asthma in asthmatic patients who are sensitive to conventional NSAIDs. These selective inhibitors of COX-2 may also be used in treating Alzheimer's disease and osteoporosis of women after menopause.

DESCRIPTION OF RETATED ART

U.S. Pat. No. 6,077,850 (G. D. Searle) discloses 1,2-dihydroquinoline derivatives for use in treating cyclooxygenase-2 mediated disorders.

U.S. Pat. No. 6,069,151 (Darwin Discovery, Ltd.) discloses quinolines and their therapeutic usee.

U.S. Pat. No. 5,962,531 (Syntex USA, Inc) discloses 5-aroylnaphthalene derivatives as anti-inflammatory agents.

U.S. Pat. No. 5,221,677 (Imperial Chemical Industries PLC) discloses quinoline or isoquinoline derivatives as 5-lipoxygenase inhibitors.

SUMMARY OF THE INVENTION

In a first aspect, this invention provides compounds selected from the group of compounds represented by Formula I:

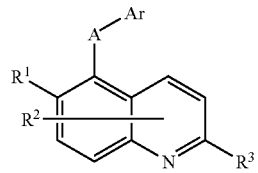

wherein:

A is a $CH_2$, $CH(OH)$, $C(O)$, $C=NOR^4$, $NR^5$, O, S, S(O), or $S(O)_2$ where $R^4$ is hydrogen or alkyl and $R^5$ is hydrogen, alkyl, or acyl;

Ar is an optionally substituted phenyl;

$R^1$ is hydrogen, alkyl, alkenyl, alkynyl, haloalkyl, heteroalkyl, cycloalkyl, cycloalkylalkyl, alkoxy, alkenyloxy, cycloalkyloxy, cycloalkylalkyloxy, haloalkyloxy, hydroxyalkyloxy, alkoxyalkyloxy, alkylsulfanyl, alkylsulfinyl, alkylsulfonyl, cycloalkylthio, cycloalkylalkylthio, hydroxy, halo, cyano, $—NR^9R^{10}$, $—OCONR^9R^{10}$, or $—OSO_2R^{11}$ where $R^9$ and $R^{10}$ are each independently selected from hydrogen, alkyl, and acyl; and $R^{11}$ is selected from alkyl, cycloalkyl, and haloalkyl;

$R^2$ is hydrogen, alkyl, alkenyl, alkoxy, hydroxy, halo, haloalkyl, heteroalkyl, alkylsulfanyl, alkylsulfinyl, alkylsulfonyl, nitro, cyano, or $—NR^9R^{10}$ where $R^9$ and $R^{10}$ are each independently selected form the respective group described for $R^9$ and $R^{10}$ previously; it is understood that, as indicated in Formula I, $R^2$ represents substitution of any one of carbons C3, C4, C7 or C8;

$R^3$ is $—SR^{12}$, $—SOR^{12}$, $—SO_2R^{12}$, or $—SO_2NR^{13}R^{14}$ wherein $R^{12}$ is alkyl, hydroxyalkyl, alkoxyalkyl, aminoalkyl, mono or dialkylaminoalkyl, carboxyalkyl, or alkoxycarbonylalkyl;

$R^{13}$ is hydrogen or alkyl, and $R^{14}$ is hydrogen, alkyl, cycloalkyl, cycloalkylalkyl, hydroxyalkyl, alkoxyalkyl, alkoxycarbonylalkyl, aminoalkyl, aryl, or aralkyl; or $R^{13}$ and $R^{14}$ together with the nitrogen atom to which they are attached form a heterocycloamino group; and prodrugs, individual isomers, mixtures of isomers, and pharmaceutically acceptable salts thereof.

In a second aspect, this invention provides pharmaceutical compositions containing a therapeutically effective amount of a compound of Formula I or its pharmaceutically acceptable salt and a pharmaceutically acceptable excipient.

In a third aspect, this invention provides a method of treatment of a disease, in particular an inflammatory and autoimmune disease, in a mammal treatable by administration of a prostaglandin G/H synthase inhibitor, comprising administration of a therapeutically effective amount of a compound of Formula I or its pharmaceutically acceptable salt.

In a fourth aspect, this invention provides processes for preparing compounds of Formula I.

DETAILED DESCRIPTION OF THE INVENTION

Definitions

Unless otherwise stated, the following terms used in the specification and claims have the meanings given below:

"Acyl" means the group —C(O)R', where R' is hydrogen, alkyl, cycloalkyl, cycloalkylalkyl, phenyl or phenylalkyl, wherein the phenyl group can be optionally substituted.

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Alkoxycarbonylalkyl" means a radical —$R^aC(O)R^b$ where $R^a$ is an alkylene group as defined above and $R^b$ is an alkoxy group as defined above e.g., methoxycarbonylethyl, ethoxycarbonylbutyl, and the like.

"Alkylsulfanyl" or "alkylthio" means a radical —SR where R is hydrogen or alkyl as defined herein, e.g., methylsulfanyl, ethylsulfanyl, and the like.

"Alkylsulfinyl" means a radical —S(O)R where R is hydrogen or alkyl as defined herein, e.g., methylsulfinyl, ehtylsulfinyl, and the like.

"Alkylsulfonyl" means a radical —$S(O)_2R$ where R is hydrogen or alkyl as defined herein, e.g., methylsulfonyl, ehtylsulfonyl, and the like.

"Aryl" means a monovalent monocyclic or bicyclic aromatic radical of 6 to 10 ring atoms which is substituted independently with one to five substituents, preferably one, two, or three substituents selected from alkyl, cycloalkyl, cycloalkylalkyl, halo, nitro, cyano, hydroxy, alkoxy, amino, acylamino, alkylamino, dialkylamino, haloalkyl, haloalkoxy, heteroalkyl, —COR (where R is hydrogen, alkyl, cycloalkyl, cycloalkyl-alkyl, phenyl or phenylalkyl), —$(CR'R'')_n$—COOR (where n is an integer from 0 to 5, R' and R'' are independently hydrogen or alkyl, and R is hydrogen, alkyl, cycloalkyl, cycloalkylalkyl, phenyl or phenylalkyl) or —$(CR'R'')_n$—$CONR^aR^b$ (where n is an integer from 0 to 5, R' and R'' are independently hydrogen or alkyl, and $R^a$ and $R^b$ are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the derivatives thereof.

"Aralkyl" means a radical —$R^aR^b$ where $R^a$ is an alkylene group and $R^b$ is an aryl group as defined herein, e.g., benzyl, phenylethyl, 3-(3-chlorophenyl)-2-methylpentyl, and the like.

"Aralkenyl" means a radical —$R^aR^b$ where $R^a$ is an alkenylene group and $R^b$ is an aryl group as defined herein, e.g., 3-phenyl-2-propenyl, and the like.

"Cycloalkyl" means a saturated monovalent cyclic hydrocarbon radical of three to seven ring carbons. The cycloalkyl may be optionally substituted independently with one, two, or three substituents selected from alkyl, optionally substituted phenyl, or —C(O)R (where R is hydrogen, alkyl, haloalkyl, amino, acylamino, mono-alkylamino, di-alkylamino, hydroxy, alkoxy, or optionally substituted phenyl). More specifically, the term cycloalkyl includes, for example, cyclopropyl, cyclohexyl, phenylcyclohexyl, 4-carboxycyclohexyl, 2-carboxamidocyclohexyl, 2-dimethylaminocarbonyl-cyclohexyl, and the like.

"Cycloalkylalkyl" means a radical —$R^aR^b$ where $R^a$ is an alkylene group and $R^b$ is a cycloalkyl group as defined herein, e.g., cyclopropylmethyl, cyclohexylpropyl, 3-cyclohexyl-2-methylpropyl, and the like.

"Haloalkyl" means alkyl substituted with one or more same or different halogen atoms, e.g., —$CH_2Cl$, —$CF_3$, —$CH_2CF_3$, —$CH_2CCl_3$, and the like, and further includes those alkyl groups such as perfluoroalkyl in which all hydrogen atoms are replaced by fluorine atoms.

"Heteroalkyl" means an alkyl radical as defined herein with one, two or three substituents independently selected from —$OR^a$, —$NR^bR^c$, and —$S(O)_nR^d$ (where n is an integer from 0 to 2), with the understanding that the point of attachment of the heteroalkyl radical is through a carbon atom of the heteroalkyl radical. $R^a$ is hydrogen, alkyl, cycloalkyl, cycloalkylalkyl, aryl, aralkyl, alkoxycarbonyl, aryloxycarbonyl, or carboxamido. $R^b$ is hydrogen, alkyl, cycloalkyl, cycloalkylalkyl, aryl or aralkyl. $R^c$ is hydrogen, alkyl, cycloalkyl, cycloalkylalkyl, aryl, aralkyl, alkoxycarbonyl, aryloxycarbonyl, carboxamido, mono- or dialkylcarbamoyl or alkylsulfonyl, $R^d$ is hydrogen (provided that n is 0), alkyl, cycloalkyl, cycloalkylalkyl, aryl, aralkyl, amino, monoalkylamino, dialkylamino, or hydroxyalkyl. Representative examples include, for example, 2-hydroxyethyl, 2,3-dihydroxypropyl, 2-methoxyethyl, benzyloxymethyl, 2-methylsulfonyl-ethyl.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl. Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents selected from alkyl, cycloalkyl, cycloalkylalkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl, —$(CR'R'')_n$—COOR (where n is an integer from 0 to 5, R' and R'' are independently hydrogen or alkyl, and R is hydrogen, alkyl, cycloalkyl, cycloalkylalkyl, phenyl or phenylalkyl), or —$(CR'R'')_n$—$CONR^aR^b$ (where n is an integer from 0 to 5, R' and R'' are independently hydrogen or alkyl, and $R^a$ and $R^b$ are, independently of each other, hydrogen, alkyl, cycloalkyl, cycloalkylalkyl, phenyl or phenylalkyl).

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g. acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynahthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of Formula I, and the like.

"Protecting group" refers to a grouping of atoms that when attached to a reactive group in a molecule masks, reduces or prevents that reactivity. Examples of protecting groups can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl and trityl ethers, as well as alkyl ethers, tetrahydropyranyl ethers, trialkylsilyl ethers, and allyl ethers.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Optional" or "optionally" in the above definitions means that the subsequently described event or circumstance may but need not occur, and that the description includes instances where the event or circumstance occurs and instances in which it does not. For example, "heterocyclo group optionally mono- or di substituted with an alkyl group" means that the alkyl may but need not be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn, Ingold and Prelog, (Cahn et al. *Angew. Chem. Inter.* Edit., 5, 385; (1966) errata 511; Cahn et al. *Angew. Chem.,* 78, 413; (1966) Cahn and Ingold *J. Chem. Soc.* (London), 612; (1951) Cahn et al. *Experientia,* 12, 81; (1956), Cahn, *J. Chem. Educ.,* 41, 116, (1964)) or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing equal proportions of the enantiomers is called a "racemic mixture".

The compounds of this invention may exist in stereoisomeric form if they possess one or more asymmetric centers. In addition, double bonds present in compounds of this invention may be either the E or Z configuration. Unless otherwise indicated, the description is intended to include individual stereoisomers as well as mixtures. Similarly, it is appreciated that the description includes individual double bond isomers as well as mixtures. The methods for the determination of stereochemistry and the separation of stereoisomers are well-known in the art (see discussion in Chapter 4 of "Advanced Organic Chemistry", 4th edition J. March, John Wiley and Sons, New York, 1992).

Throughout the application the following abbreviations are used with the following meanings:
DIBAL Diisobutylaluminum hydride
DMF N,N-Dimethylformamide
DMSO Dimethylsulfoxide
EtOAc Ethyl Acetate
HMPA Hexamethylphosphoric triamide
HPLC High pressure liquid chromatography
MCPBA m-Chloroperbenzoic acid
MHz Megahertz
MS Mass Spectrum
NMR Nuclear Magnetic Resonance
OXONE™ Potassium peroxymonosulfate
PCC Pyridinium chlorochromate
PIFA Bis(trifluoroacetoxy)iodobenzene
TFA Trifluoroacetic acid
THF Tetrahydrofuran
TLC Thin layer chromatography Nomenclature The naming and numbering of the compounds of this invention is illustrated below.

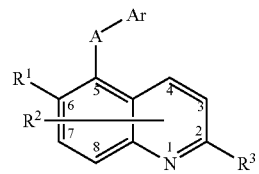

Formula I

In general, the nomenclature used in this Application is based on AUTONOM™ v.4.0, a Beilstein Institute computerized system for the generation of IUPAC systematic nomenclature.

Representative Compounds of this Invention are as Follows:
Compounds of Formula I wherein $R^1$, $R^2$, $R^3$, A, and Ar are as defined below:

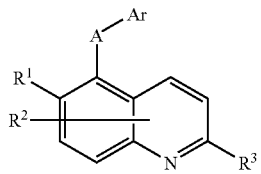

Formula I

| Cpd # | $R^1$ | $R^2$ | $R^3$ | A | Ar | MS. $[m + H]^+$ |
|---|---|---|---|---|---|---|
| 102 | methoxy | H | methylsulfonyl | —S— | 4-fluorophenyl | 364 |
| 103 | methoxy | H | methylsulfonyl | —S— | 4-chlorophenyl | 380 |
| 104 | methoxy | H | methylsulfonyl | —S— | 2-chlorophenyl | 380 |
| 101 | methoxy | H | methylsulfonyl | —S— | 2,4-difluorophenyl | 382 |
| 105 | methoxy | H | methylsulfonyl | —S— | 2-chloro-4-fluorophenyl | 398 |
| 106 | methoxy | H | methylsulfonyl | —S— | 4-bromophenyl | 425 |
| 107 | methoxy | H | methylsulfonyl | —S— | 2,4-dichlorophenyl | 415 |
| 202 | methoxy | H | methylsulfonyl | —C(O)— | 2-chlorophenyl | 376 |
| 201 | methoxy | H | methylsulfonyl | —C(O)— | 4-methoxyphenyl | 372 |
| 301 | methoxy | H | methylsulfonyl | —S(O)— | 2,4-difluorophenyl | 398 |
| 110 | methoxy | H | methylsulfonyl | —S— | 4-methoxyphenyl | 376 |
| 108 | methoxy | H | methylsulfonyl | —S— | 2,3,4,5,6-pentafluorophenyl | 436 |
| 109 | methoxy | H | methylsulfonyl | —S— | phenyl | 346 |
| 401 | hydroxy | H | methylsulfonyl | —S— | 4-fluorophenyl | 350 |
| 501 | CF$_3$SO$_2$O— | H | methylsulfonyl | —S— | 4-fluorophenyl | 482 |
| 111 | methoxy | H | methylsulfonyl | —S— | 2-fluoro-4-methoxyphenyl | 394 |
| 112 | methoxy | H | methylsulfonyl | —S— | 2-chloro-4-methoxyphenyl | 410 |
| 702 | methoxy | H | methylsulfonyl | —O— | 2-fluoro-4-methanesulfonylphenyl | 426 |
| 711 | methoxy | H | methylsulfinyl | —O— | 4-fluorophenyl | 332 |
| 703 | methoxy | H | methylsulfonyl | —O— | 4-fluorophenyl | 348 |
| 602 | methoxy | H | methylsulfonyl | —CH$_2$— | 4-fluorophenyl | 346 |
| 704 | methoxy | H | methylsulfonyl | —O— | 2-chloro-4-methoxyphenyl | 394 |
| 601 | methoxy | H | methylsulfonyl | —CH$_2$— | 2,4-difluorophenyl | 364 |
| 609 | methoxy | H | methylsulfinyl | —CH$_2$— | 2,4-difluorophenyl | 348 |
| 701 | methoxy | H | methylsulfonyl | —O— | 2,4-difluorophenyl | 366 |
| 603 | methoxy | H | methylsulfonyl | —CH$_2$— | 4-ethoxyphenyl | 346 |
| 604 | methoxy | H | methylsulfonyl | —CH$_2$— | 2-fluorophenyl | 372 |
| 203 | methoxy | H | methylsulfonyl | —C(O)— | 4-fluorophenyl | 360 |
| 602 | hydroxy | H | methylsulfonyl | —CH$_2$— | 4-fluorophenyl | 332 |

-continued

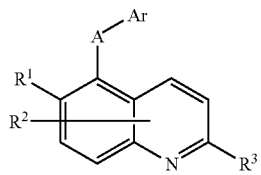

Formula I

| Cpd # | R¹ | R² | R³ | A | Ar | MS. [m + H]⁺ |
|---|---|---|---|---|---|---|
| 606 | methoxy | H | methylsulfonyl | —CH₂— | 4-methoxyphenyl | 358 |
| 605 | methoxy | H | methylsulfonyl | —CH₂— | 4-methylphenyl | 342 |
| 607 | methoxy | H | methylsulfonyl | —CH₂— | 4-chlorophenyl | 362 |
| 113 | methoxy | H | methylsulfonyl | —S— | 2-methoxy-4-fluorophenyl | 394 |
| 204 | methoxy | H | methylsulfonyl | —C(O)— | 2-fluorophenyl | 360 |
| 205 | methoxy | H | methylsulfonyl | —C(O)— | 2,4-difluorophenyl | 378 |
| 710 | methoxy | H | methylsufinyl | —O— | 2,4-difluorophenyl | 350 |
| 705 | methoxy | H | methylsulfonyl | —O— | 4-ethoxyphenyl | 374 |
| 706 | methoxy | H | methylsulfonyl | —O— | phenyl | 330 |
| 206 | methoxy | H | methylsulfonyl | —C(O)— | 4-ethoxyphenyl | 386 |
| 207 | methoxy | H | methylsulfonyl | —C(O)— | 4-chlorophenyl | 376 |
| 707 | methoxy | H | methylsulfonyl | —O— | 2-fluorophenyl | 348 |
| 608 | methoxy | H | methylsulfanyl | —CH₂— | 2,4,-difluorophenyl | 332 |
| 712 | methoxy | H | methylsulfanyl | —O— | 2,4,-difluorophenyl | 334 |
| 114 | methoxy | H | methylsulfonyl | —S— | 2,6-difluorophenyl | 382 |
| 211 | methoxy | H | methylsulfinyl | —C(O)— | 4-fluorophenyl | 344 |
| 208 | methoxy | H | methylsulfonyl | —C(O)— | 3-chloro-2-fluoro-6-methoxyphenyl | 424 |
| 214 | methoxy | H | methylsulfinyl | —C(O)— | 3-chloro-2-fluoro-6-methoxyphenyl | 408 |
| 708 | methoxy | H | methylsulfonyl | —O— | 2,6-difluorophenyl | 366 |
| 209 | methoxy | H | methylsulfonyl | —C(O)— | 3-bromo-2,6-difluorophenyl | 457 |
| 210 | methoxy | H | methylsulfonyl | —C(O)— | 2,6-difluorophenyl | 378 |
| 212 | methoxy | H | methylsulfinyl | —C(O)— | 4-chlorophenyl | 360 |
| 213 | methoxy | H | methylsulfinyl | —C(O)— | 4-ethoxyphenyl | 370 |
| 709 | methoxy | H | methylsulfonyl | —O— | 2-fluoro-6-methanesulfonylphenyl | 426 |

PREFERRED EMBODIMENTS

While the broadest definition of this invention is set forth in the Summary of the Invention, certain compounds of Formula I are preferred.

A. In certain preferred embodiments A is —S—. Within the foregoing preferred embodiment, another preferred group of compounds is that wherein:
  R¹ is alkyl, alkoxy, hydroxy, halogen, or cyano;
  R² is hydrogen or methyl; and
  R³ is $S(O)_{0-2}R^{12}$ where $R^{12}$ is alkyl.

Within the foregoing preferred embodiment, another preferred group of compounds is that wherein Ar is selected from the group consisting of an unsubstituted phenyl, a 4-substituted phenyl, and a 2-substituted phenyl. An additional preferred group of compounds is that wherein Ar is a disubstituted phenyl, such as 2,4-disubstituted phenyl or 3,4-disubstituted phenyl.

Within the foregoing preferred embodiment another preferred group of compounds is that wherein Ar is a phenyl optionally substituted at one or more positions, preferably with one to two substituents independently selected from the group consisting of fluoro, chloro, bromo, ethoxy and methoxy.

B. In other preferred embodiments A is —C(O)—. Within the foregoing preferred embodiment, another preferred group of compounds is that wherein:
  R¹ is alkyl, alkoxy, hydroxy, halogen or cyano;
  R² is hydrogen or methyl; and
  R³ is $S(O)_{0-2}R^{12}$ where $R^{12}$ is alkyl.

Within the foregoing preferred embodiment, another preferred group of compounds is that wherein Ar is selected from the group consisting of an unsubstituted phenyl, a 4-substituted phenyl, and a 2-substituted phenyl. An additional preferred group of compounds is that wherein Ar is a disubstituted phenyl, such as 2,4-disubstituted phenyl or 3,4-disubstituted phenyl.

Within the foregoing preferred embodiment another preferred group of compounds t is that wherein Ar is a phenyl optionally substituted at one or more positions with a substitutent or substitutents independently selected from the group consisting of fluoro, chloro, bromo, ethoxy and methoxy.

C. In additional preferred embodiments A is —O—. Within the foregoing preferred embodiment, another preferred group of compounds is that wherein:
  R¹ is alkyl, alkoxy, hydroxy, halogen or cyano;
  R² is hydrogen or methyl; and
  R³ is $S(O)_{0-2}R^{12}$ where $R^{12}$ is alkyl.

Within the foregoing preferred embodiment, another preferred group of compounds is that wherein Ar is selected from the group consisting of an unsubstituted phenyl, a 4-substituted phenyl, and a 2-substituted phenyl. An additional preferred group of compounds is that wherein Ar is a disubstituted phenyl, such as 2,4-disubstituted phenyl or 3,4-disubstituted phenyl.

Within the foregoing preferred embodiment another preferred group of compounds is that wherein Ar is a phenyl optionally substituted at one or more positions with a substitutent or substitutents independently selected from the group consisting of fluoro, chloro, bromo, ethoxy and methoxy.

D. In additional preferred embodiments A is —$CH_2$—.
Within the foregoing preferred embodiment, another preferred group of compounds is that wherein:
$R^1$ is alkyl, alkoxy, hydroxy, halogen or cyano;
$R^2$ is hydrogen or methyl; and
$R^3$ is $S(O)_{0-2}R^{12}$ where $R^{12}$ is alkyl.

Within the foregoing preferred embodiment, another preferred group of compounds is that wherein Ar is selected from the group consisting of an unsubstituted phenyl, a 4-substituted phenyl, and a 2-substituted phenyl. An additional preferred group of compounds is that wherein Ar is a disubstituted phenyl, such as 2,4-disubstituted phenyl or 3,4-disubstituted phenyl.

Within the foregoing preferred embodiment another preferred group of compounds is that wherein Ar is a phenyl optionally substituted at one or more positions with a substitutent or substitutents independently selected from the group consisting of fluoro, chloro, bromo, ethoxy and methoxy.

E. In additional preferred embodiments, preferred compounds of Formula I are those in which $R^1$ is hydroxy, alkoxy or alkyl, $R^2$ is hydrogen or alkyl, $R^3$ is alkylsulfanyl, alkylsulfinyl or alkylsulfonyl, and Ar is unsubstituted, monosubstituted, or disubstituted phenyl. Even more preferred are compounds of Formula I are those in which $R^1$ is methoxy, $R^2$ is hydrogen, $R^3$ is alkylsulfonyl, and Ar is a mono or disubstituted phenyl.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989); *Organic Reactions*, Volumes 1–40 (John Wiley and Sons, 1991), *March's Advanced Organic Chemistry*, (John Wiley and Sons, 4th Edition) and *Larock's Comprehensive Organic Transformations* (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including the measurement of hysical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

A person of ordinary skill in the art will have no difficulty, having regard to that skill and this disclosure, in determining how to synthesize compounds of this invention.

Preparation of Compounds of Formula I

Schemes A, B, C, and D describe methods to prepare the compounds of Formula I.

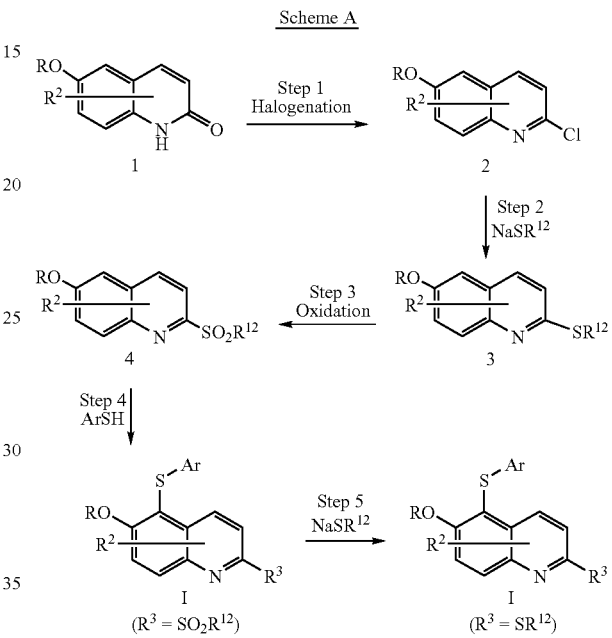

Scheme A

Scheme A is the synthesis of a compound of Formula I wherein A is —S—, —S(O)—, or $SO_2$; $R^3$ is —$S(O)_{0-2}R^{12}$ (wherein $R^{12}$ is alkyl); R is alkyl, and $R^2$ and Ar are as defined in the Summary of the Invention.

In Step 1, a quinolone of Formula 1 (wherein R is alkyl) is halogenated with an inorganic acid halide such as $POCl_3$ to give a chloroquinoline of Formula 2. In general, the compounds of Formula 1 are commercially available or can be readily synthesized by those of ordinary skill in the art, see e.g., DeRuiter et al, *J. Med Chem.*, 29, 10; 2021–2028 (1986).

In Step 2, the chloroquinoline is modified by displacement with a thiolate ion of general formula $NaSR^{12}$ (wherein $R^{12}$ is alkyl) to provide a quinoline sulfide of Formula 3. Suitable solvents for the reaction are polar aprotic solvents such as DMF, DMSO, HMPA, and the like. This reaction can also be carried out with compounds of Formula 2 wherein the 2 position is a leaving group other than chlorine, such as for example alkanesulfonyloxy, arenesulfonyloxy, alkylcarbonyloxy, arylcarbonyloxy, mesyloxy, tosyloxy, trifluoromethanesulfonyloxy, aryloxy, methoxy, or N,O-dimethylhydroxylamino.

In Step 3, oxidation of the quinoline sulfide of Formula 3 with a suitable amount of oxidizing agent, such as OXONE™, MCPBA, and the like, provides a quinoline sulfone of Formula 4. Suitable solvents for the reaction are alcohols (such as methanol and ethanol) or halogenated solvents (such as dichloromethane, chloroform, and the like).

In Step 4, the quinoline sulfoxide or the quinoline sulfone are coupled with an aryl thiol of general formula ArSH to provide a compound of Formula I wherein A is —S— and $R^3$ is —$SO_2R^{12}$ wherein $R^{12}$ is alkyl.

In Step 5, the compound of Formula I wherein $R^3$ is —$SO_2R^{12}$ may then be converted to the quinoline sulfide of Formula I wherein $R^3$ is —$SR^{12}$ by treatment with a sodium thiolate of Formula $NaSR^{12}$ in suitable solvents such as polar aprotic solvents, e.g. DMF, DMSO and the like.

As an additional step the compound of Formula I can be further oxidized with a suitable amount of OXONE™, MCPBA, and the like to provide a compound of Formula I wherein A is —S(O)— or —$SO_2$—. Similarly, oxidation can provide a compound of Formula I, wherein $R^3$ is $S(O)R^{12}$.

Using synthetic techniques well known in the art, the —OR (wherein R is alkyl) substituent at the 6-position of the quinoline can be converted to any one of the other claimed substituents for $R^1$.

Invention. An alternative synthesis of a compound of Formula I wherein A is —$CH_2$— is described in Scheme D.

In Step 1, the quinoline sulfone of Formula 5 (wherein R is alkyl, see e.g. Hayashi et al., Chem. Abstr.; 87 167846; (1977)) is brominated with bromine. After stirring, the above reaction mixture is poured into a solution of a base (such as sodium bicarbonate and the like) and sodium thiosulfate to provide a bromo quinoline sulfone of Formula 6. Suitable solvents for this reaction are halogenated hydrocarbons, such as dichloromethane, dichloroethane, and the like.

In Step 2, the bromo quinoline sulfone 6 is treated with a thiolate ion of general formula $NaSR^{12}$ (wherein $R^{12}$ is alkyl) to provide a bromo quinoline sulfide of Formula 7. Suitable solvents for this reaction are polar aprotic solvents such as DMF, DMSO, HMPA, tetraglyme, and the like.

In Step 3, the bromo quinoline sulfide 7 is initially treated with t-BuLi. To this reaction mixture is added an aryl aldehyde of general formula ArCHO to provide a secondary

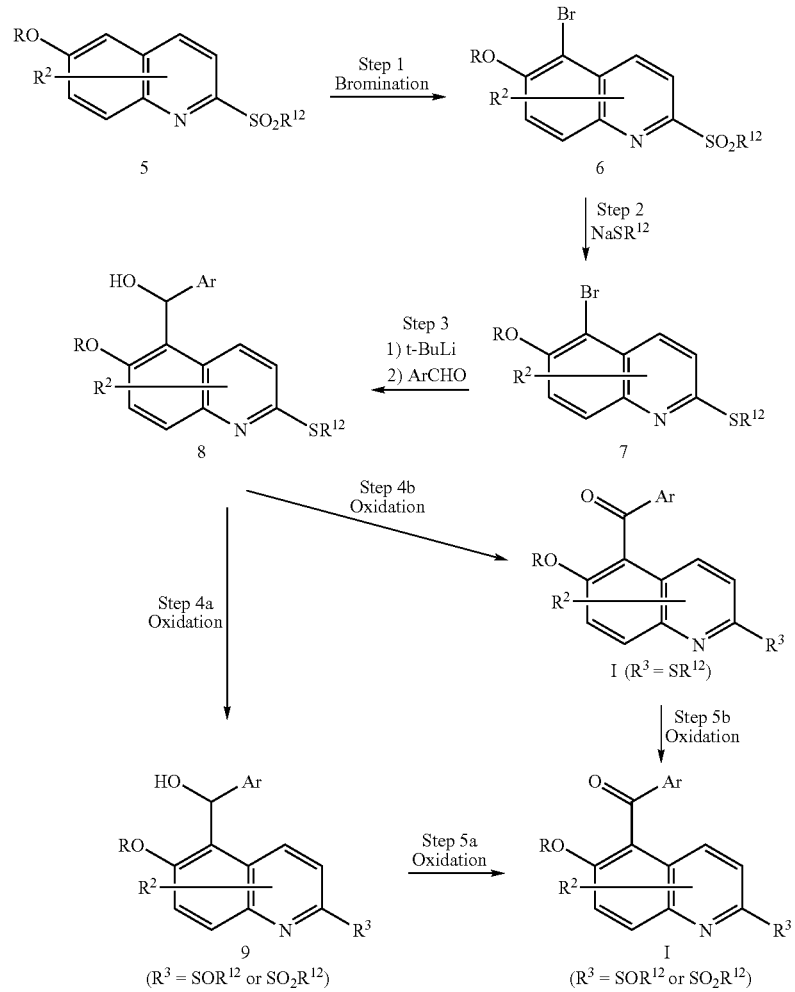

Scheme B

Scheme B is illustrative of the synthesis of a compound of Formula I wherein A is —$CH_2$—, —C(O)—, CH(OH), or C=$NOR^4$; $R^3$ is —$S(O)_{0-2}R^{12}$ (wherein $R^{12}$ is alkyl); and $R^1$, $R^2$, and Ar are as defined in the Summary of the alcohol quinoline sulfide of Formula 8. Suitable solvents for this reaction are Lewis bases such as THF, diethyl ether, dioxane, and the like. This reaction is carried out at approximately −78° C. to room temperature.

At this point, one of two synthetic routes can be taken depending on what is desired as the substituent at $R^3$.

In Step 4a, oxidation of the secondary alcohol quinoline sulfide of Formula 8 with a suitable amount of oxidizing agent, such as OXONE™, MCPBA, and the like, provides a secondary alcohol quinoline sulfoxide or a secondary alcohol quinoline sulfone of Formula 9. Suitable solvents for the reaction are alcohols, such as methanol, ethanol, and the like.

In Step 5a, oxidation of the secondary alcohol quinoline sulfoxide or the secondary alcohol quinoline sulfone with a mild oxidizing agent such as PCC, $MnO_2$, and the like, provides a compound of Formula I wherein A is —C(O)— and $R^3$ is —S(O)$_{1-2}R^{12}$. Suitable solvents for this reaction are halogenated hydrocarbons, such as dichloromethane, dichloroethane, and the like.

Using synthetic techniques well known in the art, the —OR (wherein R is alkyl) substituent at the 6-position of the quinoline can be converted to any one of the other claimed substituents for $R^1$.

As an alternative, in Step 4b a Swern oxidation is used to oxidize the secondary alcohol quinoline sulfide of Formula 8. In this method, oxidation of the alcohol is carried out with dimethyl sulfoxide and oxalyl chloride to provide a compound of Formula I wherein A is —C(O)— and $R^3$ is —$SR^{12}$. Suitable solvents for the reaction are halogenated hydrocarbons, such as dichloromethane, dichloroethane, and the like. In Step 5b compound of Formula I (wherein $R^3$ is —S(O)$_{1-2}R^{12}$) may be obtained by oxidation of the quinoline sulfide of Formula I (wherein $R^3$ is —$SR^{12}$) with a suitable amount of oxidizing agent such as OXONE™, MCPBA, and the like Again as an additional step using synthetic techniques well known in the art, the —OR (wherein R is alkyl) substituent at the 6-position of the quinoline can be converted to any one of the other claimed substituents for $R^1$.

As an additional alternative, condensation of a compound of Formula I with a hydroxylamine ($R^4ONH_2$) gives a compound of Formula I wherein A is —C=$NOR^4$.

In another alternative, an alcohol of Formula 8 or 9 can be reduced to give a compound of Formula I wherein A is —$CH_2$—. This reduction can be performed, for example, by catalytic hydrogenation, under the reaction conditions of TFA/triethylsilane, or under radical processes.

Alternative Preparation of an Alcohol of General Formula 8:

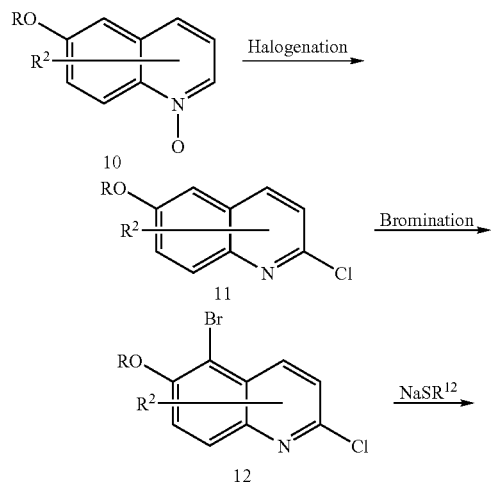

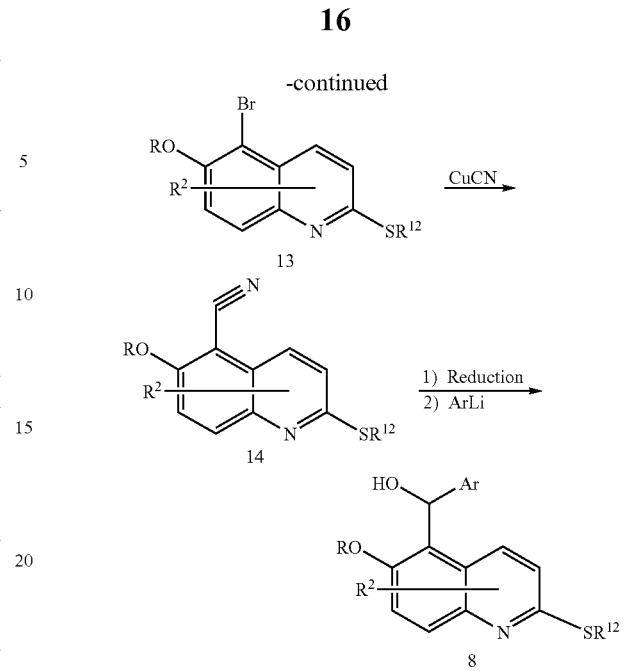

An alternative synthesis of the alcohol of general Formula 8 may be achieved by halogenation of the quinoline N-oxide of Formula 10 with an inorganic acid halide such as $POCl_3$, to give the chloroquinoline of general Formula 11. Subsequently the chloroquinoline may be further brominated to yield the 5-bromo-2-chloroquinoline of Formula 12 which may be further modified by displacement with a thiolate ion of general formula $NaSR^{12}$ to provide a quinoline bromide of general Formula 13. The quinoline bromide may be converted to the quinoline nitrile of general Formula 14 by Rosenmund-von Braun cyano-de-halogenation with cuprous cyanide, or by reaction with alkali cyanides in the presence of Pd(II) salts or under phase transfer conditions in the presence of a nickel complex, preferably with cuprous cyanide. The quinoline nitrile of general Formula 14 may be reduced with a metal hydride reducing agent, preferably with diisobutylaluminum hydride (DIBAL), and subsequently treated with a suitable organometallic aryl such as aryllithium to provide the quinoline alcohol of general Formula 8.

Scheme C

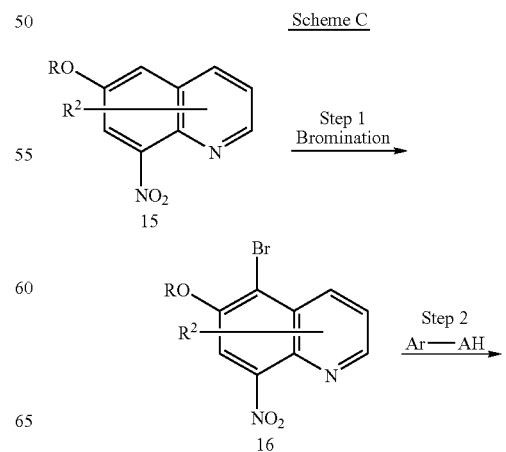

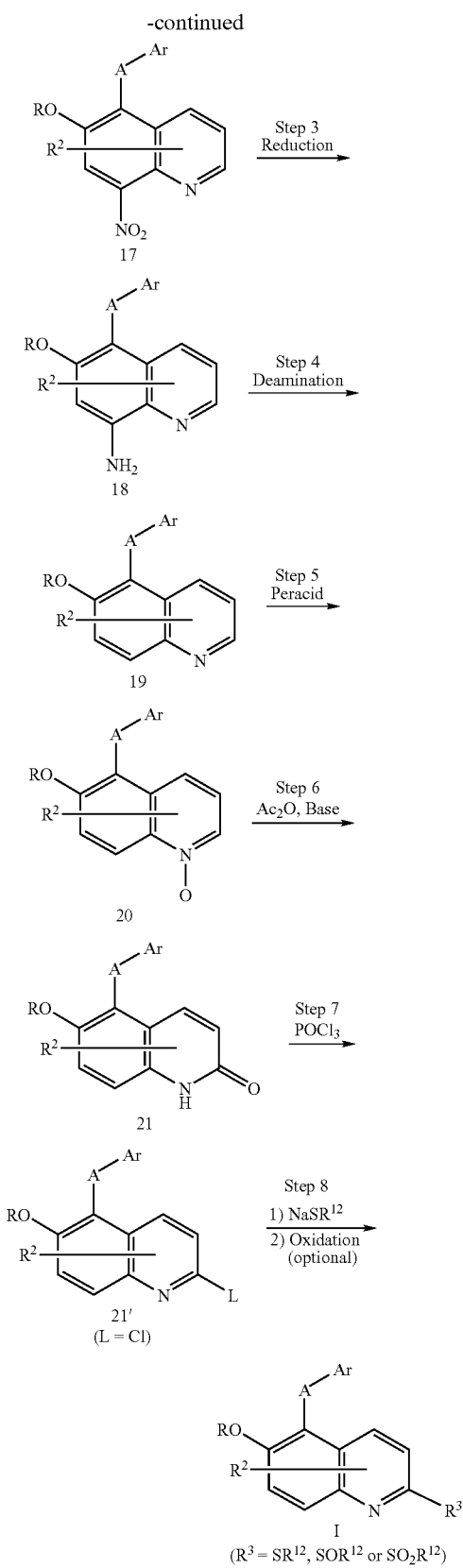

$R^{12}$ (wherein $R^{12}$ is alkyl); and $R^1$, $R^2$, and Ar are as defined in the Summary of the Invention.

In Step 1, the 8-nitroquinoline of Formula 15 (wherein R is alkyl, see e.g. Haskelberg et al., *J. Org. Chem.*, 12, 434 (1947)) is brominated with bromine to provide a 5-bromo-8-nitroquinoline of Formula 16. Suitable solvents for this reaction are halogenated hydrocarbons, such as dichloromethane, dichloroethane, and the like.

In Step 2, the 5-bromo-8-nitroquinoline is treated with a compound of general formula, Ar—AH (wherein A is —$NR^5$ or —O—) to provide a 8-nitroquinoline of Formula 17 (wherein A is —$NR^5$ or —O—).

In Step 3, the nitro group of the 8-nitroquinoline 17 is reduced using a suitable reducing agent (such as $SnCl_2$ and EtOH, palladium catalyzed hydrogenation, and the like) to provide an 8-aminoquinoline of Formula 18.

In Step 4, the amino of the 8-aminoquinoline 18 is deaminated by methods well known in the art. A preferred method may be achieved in a one step by treatment with an alkyl nitrite in a suitable solvent such as DMF or boiling THF. This reaction provides the quinoline of Formula 19.

In Step 5, the quinoline of Formula 19 is treated with a peracid or with hydrogen peroxide to form the quinoline N-oxide of Formula 20. Suitable solvents include acetic acid and the like.

In Step 6, the quinoline N-oxide 20 is treated with acetic anhydride and a base (such as NaOH, KOH, and the like) to provide a 2-quinolone of Formula 21.

In Step 7, chlorine as leaving group L is introduced to the 2-quinolone 21 by halogenation with an inorganic acid halide such as $POCl_3$, to give a chloroquinoline 21'. The leaving group L at the 2-position of the quinoline can also be, for example, alkanesulfonyloxy, arenesulfonyloxy, alkylcarbonyloxy, arylcarbonyloxy, mesyloxy, tosyloxy, trifluoromethanesulfonyloxy, aryloxy, methoxy, or N,O-dimethylhydroxylamino.

In Step 8, the quinoline of formula 21' is treated with a thiolate ion of general formula $NaSR^{12}$. This reaction provides a compound of Formula I wherein $R^3$ is —$SR^{12}$ (wherein $R^{12}$ is alkyl). Optionally, this compound may be oxidized with a suitable amount of oxidizing agent such as as OXONE™, MCPBA, and the like, to provide a compound of Formula I wherein $R^3$ is —$SOR^{12}$ or —$SO_2R^{12}$" (wherein $R^{12}$ is alkyl). Suitable solvents for the oxidation are alcohols, such as methanol, ethanol, and the like.

Using synthetic techniques well known in the art the —OR (wherein R is alkyl) substituent at the 6-position of the quinoline can be converted to any one of the other claimed substituents for $R^1$.

Scheme C is illustrative the synthesis of a compound of Formula I wherein A is —$NR^5$— or —O—; $R^3$ is —$S(O)_{0-}$ Scheme D

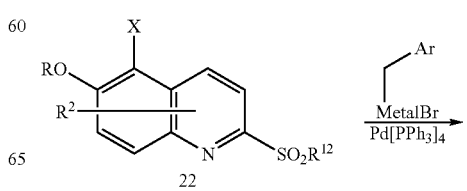

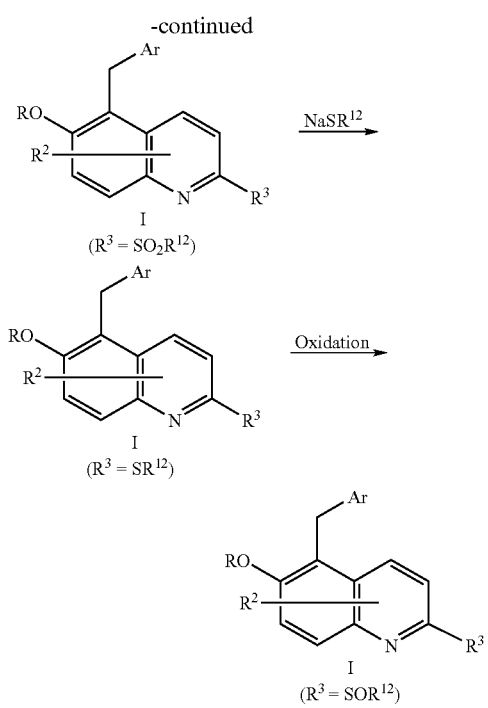

Scheme D is illustrative of an alternative synthesis of a compound of Formula I wherein A is $CH_2$; and $R^1$, $R^2$, and Ar are as defined in the Summary of the Invention. An alternative synthesis is described herein in Scheme B.

The quinoline sulfone compound 22 wherein X is a halogen, more preferably a bromide, may be treated with an optionally substituted benzyl metal bromide, wherein the metal is preferably zinc or magnesium, and more preferably zinc, in the presence of tetrakis(triphenylphosphine)palladium in an inert solvent such as THF to afford a compound of Formula I ($R^3$=—$SO_2R^{12}$).

Optionally the quinoline sulfone of Formula I ($R^3$=—$SO_2R^{12}$) may then be converted to the quinoline sulfide I ($R^3$=—$SR^{12}$) by treatment with sodium thiomethoxide in suitable solvents such as polar aprotic solvents, e.g. DMF, DMSO, HMPA, tetraglyme, and the like. The sulfide may be further optionally oxidized with two equivalents of a suitable oxidizing agent such as OXONE™ to provide the quinoline sulfoxide of Formula I ($R^3$=—$SOR^{12}$).

Using synthetic techniques well known in the art the —OR (wherein R is alkyl) substituent at the 6-position of the quinoline can be converted to any one of the other claimed substituents for $R^1$.

General Utility

The compounds of the invention are inhibitors of prostaglandin G/H Synthase I and II (COX I and COX II), especially COX II, in vitro, and as such are expected to possess both anti-inflammatory and analgesic properties in vivo. See, for example, Goodman and Gilmans's "The Pharmacological Basis of Therapeutics", Ninth Edition, McGraw Hill, New York, 1996, Chapter 27. The compounds, and compositions containing them, are therefore useful as anti-inflammatory and analgesic agents in mammals, especially humans. They find utility in the treatment of fever, inflammation, and pain caused by conditions such as rheumatic fever, symptoms associated with influenza or other viral infections, low back and neck pain, dysmenorrhoea, headache, dental pain, sprains, strains, sports injuries, bursitis, tendonitis, myositis, synovitis, arthritis (rheumatoid arthritis and osteoarthritis), gout, ankylosing spondylitis, burns, or injuries. They maybe used to inhibit prostanoid-induced smooth muscle contractions (e.g., in the treatment of dysmenorrhoea, premature labor, and asthma) and to treat autoimmune disorders (such as systemic lupus erythematosus and type I diabetes).

As inhibitors of prostaglandin G/H Synthase, the compounds of this invention are also expected to be useful in the prevention and treatment of cancer, in particular colon cancer. It has been shown that COX-2 gene expression is upregulated in human colorectal cancers and that drugs that inhibit prostaglandin G/H Synthase are effective in animal models of cancer (Eberhart, C. E., et. al., *Gastroenterology*, 107, 1183–1188, (1994), and Ara, G. and Teicher, B. A., *Prostaglandins, Leukotrienes and Essential Fatty Acids*, 54, 3–16, (1996)). In addition, there is epidemiological evidence that shows a correlation between use of drugs that inhibit prostaglandin G/H synthase and a reduced risk of developing colorectal cancer, (Heath, C. W. Jr., et. al., *Cancer*, 74, No. 10, 2885–8, (1994)).

The compounds of this invention are also expected to be useful in the prevention and treatment of Alzheimer's disease. Indomethacin, an inhibitor of prostaglandin G/H synthase, has been shown to inhibit the cognitive decline of Alzheimer's patients, (Rogers, J., et. al., *Neurology*, 43, 1609, (1993)). Also, the use of drugs which inhibit prostaglandin G/H synthase has been linked epidemiologically with a delayed onset of Alzheimer's disease, (Breitner, J. C. S., et. al., *Neurobiology of Aging*, 16, No. 4, 523, (1995) and *Neurology*, 44, 2073, (1994)).

Testing

The anti-inflammatory activity of the compounds of this invention may be assayed by measuring the ability of the compound to inhibit COX I and COX II, especially COX II, in vitro, using a radiometric assay, as described in more detail in Example 9. It may also be assayed by in vivo assays such as the Rat Carrageenan Paw and Rat Air-Pouch assays, as described in more detail in Examples 10 and 11. The analgesic activity of the compounds of this invention may be assayed by in vivo assays such as the Randall-Selitto assay and the rat arthritis pain model, as described in Example 12.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula I may range from approximately 0.005–10 mg per kilogram body weight of the recipient per day; preferably about 0.05–1 mg/kg/day. Thus, for administration to a 70 kg person, the dosage range would preferably be about 3.5 mg to 400 mg per day.

In general, compounds of this invention will be administered as pharmaceutical compositions by any one of the following routes: oral, systemic (e.g., transdermal, intranasal, or by suppository), or parenteral (e.g., intramuscular, intravenous, or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula I based on the total formulation, with the balance being one or more suitable pharmaceutical excipients. Preferably, the compound is present at a level of about 1–80 wt %. Representative pharmaceutical formulations containing a compound of Formula I are described in Example 7.

EXAMPLES

The following preparations and examples are given to enable those skilled in the art to more clearly understand and to practice the present invention. They should not be considered as limiting the scope of the invention, but merely as being illustrative and representative thereof.

Example 1

5-(2,4-Difluoro-phenylsulfanyl)-2-methanesulfonyl-6-methoxy-quinoline 101

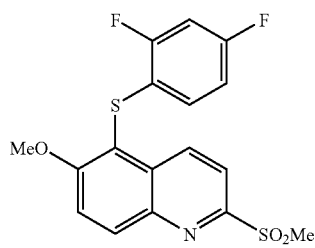

Step 1

A solution of 1.7 g of 6-methoxy-2(1H)-quinolone (10 mmoles) in 25 mL $POCl_3$ was refluxed for 2 hours. The reagent was removed under reduced pressure and the resulting gum dissolved in $CH_2Cl_2$. The solution was washed with aqueous $NaHCO_3$ to remove remaining acid, dried over $MgSO_4$, and then evaporated to afford 2-chloro-6-methoxy-quinoline as a solid.

Step 2

The 2-chloro-6-methoxy-quinoline was dissolved in 30 mL DMF and treated with 3 g NaSMe. After stirring for 2 hours the mixture was poured into water and extracted with ether. The ether was dried over $MgSO_4$ and evaporated to give 2-methylsulfanyl-6-methoxy-quinoline as a solid, (80–90% for the foregoing two steps).

Step 3

A solution of 6-methoxy-2-methylsulfanyl-quinoline (1.0 g, 5 mmoles) in 100 mL 1:1 MeOH/THF was treated with a solution of 5 g OXONE™ in 50 mL water and stirred for 2–3 hours until the oxidation is complete. The mixture is poured into water and extracted with EtOAc. The organic phase is dried and evaporated to yield 2-methanesulfonyl-6-methoxy-quinoline as a crystalline white product.

Step 4

A solution of 2-methanesulfonyl-6-methoxy-quinoline (237 mg, 1 mmole) and 2,4-difluorobenzenethiol (296 mg, 2 mmoles) was treated with PIFA (645 mg, 1.5 mmoles) and stirred for 30 min. The solution was poured into dilute NaCl solution and extracted with ethyl acetate (EtOAc). The organic layer was dried ($MgSO_4$) and evaporated. The resulting oil was crystallized to yield 5-(2,4-difluoro-phenylsulfanyl)-2-methanesulfonyl-6-methoxy-quinoline 101.; ([M+H]$^+$)=382 The yield is typically 80–90%.

In Step 4 above, replacing 2,4-difluorobenzenethiol with the following benzenethiols gives the following compounds of Formula I:

4-fluorobenzenethiol gives 5-(4-fluoro-phenylsulfanyl)-2-methanesulfonyl-6-methoxy-quinoline 102; ([M+H]$^+$)=364;

4-chlorobenzenethiol gives 5-(4-chloro-phenylsulfanyl)-2-methanesulfonyl-6-methoxy-quinoline 103; ([M+H]$^+$)=380;

2-chlorobenzenethiol gives 5-(2-chloro-phenylsulfanyl)-2-methanesulfonyl-6-methoxy-quinoline 104; ([M+H]$^+$)=380;

2-chloro-4-fluorobenzenethiol gives 5-(2-chloro-4-fluoro-phenylsulfanyl)-2-methanesulfonyl-6-methoxy-quinoline 105; ([M+H]$^+$)=398;

4-bromobenzenethiol gives 5-(4-bromo-phenylsulfanyl)-2-methanesulfonyl-6-methoxy-quinoline 106; ([M+H]$^+$)=425;

2,4-dichlorobenzenethiol gives 5-(2,4-dichloro-phenylsulfanyl)-2-methanesulfonyl-6-methoxy-quinoline 107; ([M+H]$^+$)=415;

2,3,4,5,6-pentafluorobenzenethiol gives 2-methanesulfonyl-6-methoxy-5-(2,3,4,5,6)-pentafluorophenylsulfanyl-quinoline 108; ([M+H]$^+$)=436;

benzenethiol gives 2-methanesulfonyl-6-methoxy-5-(phenyl)sulfanyl-quinoline 109; ([M+H]$^+$)=346;

4-methoxybenzenethiol gives 2-methanesulfonyl-6-methoxy-5-(4-methoxy-phenylsulfanyl)-quinoline 110; ([M+H]$^+$)=376;

2-fluoro-4-methoxybenzenethiol gives 5-(2-fluoro-4-methoxy-phenylsulfanyl)-2-methanesulfonyl-6-methoxy-quinoline 111; ([M+H]$^+$)=394;

2-chloro-4-methoxybenzenethiol gives 5-(2-chloro-4-methoxy-phenylsulfanyl)-2-methanesulfonyl-6-methoxy-quinoline 112; ([M+H]$^+$)=410;

2-methoxy-4-fluorobenzenethiol gives 5-(2-methoxy-4-fluoro-phenylsulfanyl)-2-methanesulfonyl-6-methoxy-quinoline 113; ([M+H]$^+$)=394; and 2,6-Difluorobenezenethiol gives 5-(2,6-difluoro-phenylsulfanyl)-2-methanesulfonyl-6-methoxy-quinoline 114; ([M+H]$^+$)=382.

Example 2

1-(2-Methanesulfonyl-6-methoxy-quinolin-5-yl)-1-(4-methoxy-phenyl)-methanone 201

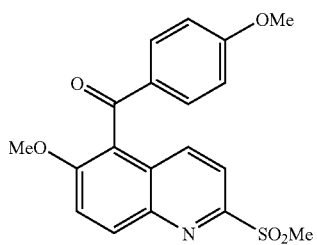

Step 1

A solution of 2-methanesulfonyl-6-methoxy-quinoline (237 mg, 1 mole) in CH$_2$Cl$_2$ was treated with 2 mmoles Br$_2$ and stirred for 1 day. The mixture was poured into a solution of NaHCO$_3$ and sodium thiosulfate. The product was extracted with CH$_2$Cl$_2$. The organic layer was dried and evaporated to afford 5-bromo-2-methanesulfonyl-6-methoxy-quinoline, 287 mg (91%), as white crystals.

Step 2

The 5-bromo-2-methanesulfonyl-6-methoxy-quinoline was dissolved in 20 mL DMF and treated with 3 eq NaSCH$_3$. After stirring 1 hour at room temperature the mixture was poured into water and extracted with ether. The crystalline product, 5-bromo-6-methoxy-2-methylsulfanyl-quinoline, was isolated in quantitative yield.

Step 3

A solution of 280 mg (1 mmole) of 5-bromo-6-methoxy-2-methylsulfanyl-quinoline in 4 mL THF was cooled to −78° C. and treated with 1.5 mL of 1.5 M t-BuLi in pentane. After stirring for 1.5 hours, 1.5 eq of p-methoxybenzaldehyde was added and the reaction allowed to warm to room temperature. After partitioning between EtOAc and water the product was purified by chromatography on silica gel (1:3 EtOAc/hexane) to afford (6-methoxy-2-methylsulfanyl-quinolin-5-yl)-(4-methoxy-phenyl)methanol (120 mg, 35%).

Step 4

(6-methoxy-2-methylsulfanyl-quinolin-5-yl)-(4-methoxy-phenyl)methanol was dissolved in 5 mL MeOH and treated with 1 g of OXONE™ in 5 mL water. After stirring 45 min. it was poured into water and the product extracted with CH$_2$Cl$_2$. The product (2-methanesulfonyl-6-methoxy-quinolin-5-yl)-(4-methoxy-phenyl)methanol was used directly in the next reaction.

Step 5

(2-Methanesulfonyl-6-methoxy-quinolin-5-yl)-(4-methoxy-phenyl)methanol was dissolved in 20 mL CH$_2$Cl$_2$ and treated with 1.5 g each Celite® and PCC. After stirring 2 hours an additional gram of PCC was added. After a further hour, the mixture was filtered to remove solids and the organic phase was washed with water. After drying and evaporation the product 1-(2-methanesulfonyl-6-methoxy-quinolin-5-yl)-1-(4-methoxy-phenyl)-methanone 201 was purified by chromatography (1:2 EtOAc/hexane). It was isolated as a foam (80 mg, 61% over two steps). ([M+H]$^+$)=372;

In Step 3 above, replacing p-methoxybenzaldehyde with the following benzaldehydes gives the following compounds of Formula I:

2-chloro-4-methoxybenzaldehyde gives 1-(2-chloro-4-methoxyphenyl)-1-(2-methanesulfonyl-6-methoxy-quinolin-5-yl)-methanone, 202 ([M+H]$^+$)=376;

3-chloro-2-fluoro-6-methoxy-benzaldehyde gives 1-(3-chloro-2-fluoro-6-methoxyphenyl)-1-(2-methanesulfonyl-6-methoxy-quinolin-5-yl)-methanone, 208 ([M+H]$^+$)=424;

3-bromo-2,6-difluoro-benzaldehyde gives 1-(3-bromo-2,6-difluoro-phenyl)-1-(2-methanesulfonyl-6-methoxy-quinolin-5-yl)-methanone, 209 ([M+H]$^+$)=457; and 2,6-difluoro-benzaldehyde gives 1-(2,6-difluoro-phenyl)-1-(2-methanesulfonyl-6-methoxy-quinolin-5-yl)-methanone, 210 ([M+H]$^+$)=378.

Alternatively the quinoline alcohol of Step 3 may be synthesized by the following steps:

Step 1a

A solution of 6-methoxyquinoline N-oxide (5.0 g, 29 mmol) in CHCl$_3$ (30 mL) was treated by slow addition of POCl$_3$ (5.3 mL, 57 mmol) at 0° C. The mixture was heated at 80° C. for 14 hours. The mixture was cooled and poured onto ice. After stirring for 30 min., the aqueous layer was adjusted to pH 9 by Na$_2$CO$_3$ addition. The mixture was extracted with CH$_2$Cl$_2$. The organic layer was worked-up. HPLC (1:10 EtOAc/hexane) gave 2.5 g (46%) of 2-chloro-6-methoxyquinoline as a white solid, (M$^+$) 193(100).

Step 2a

A solution of 2-chloro-6-methoxyquinoline (4.4 g, 22 mmol) in CH$_2$Cl$_2$ (60 mL) was treated by slow addition of Br$_2$ (3.5 mL, 11 g, 68 mmol). After 14 hours, the mixture was partitioned between NaCl and CH$_2$Cl$_2$. The aqueous layer was extracted with CH$_2$Cl$_2$. The organic layer was worked-up. HPLC (1:10 EtOAc/hexane) gave 6.1 g (99%) of 5-bromo-2-chloro-6-methoxyquinoline as a light yellow solid, (M+) 273(100).

Step 3a

A solution of 5-bromo-2-chloro-6-methoxyquinoline (6.2 g, 22 mmol) in DMF (70 mL) was treated with NaSMe (1.9 g, 27 mmol). After 6 hours, the mixture was partitioned between NaCl and EtOAc. The aqueous layer was extracted with EtOAc. The organic layer was worked-up. HPLC (1:10 EtOAc/hexane) gave 6.1 g (98%) of 5-bromo-6-methoxy-2-methylthioquinoline as a white solid, (M+) 283(100).

Step 4a

A mixture of 5-bromo-6-methoxy-2-methylthioquinoline (6.1 g, 21 mmol) and CuCN (3.7 g, 41 mmol) in DMF (80 mL) was heated at 150° C. for 14 hours. The mixture was cooled and treated sequentially with 2:1 $H_2O$/ethylenediamine (15 mL). The mixture was extracted with 1:1 EtOAc/hexane. The organic layer was worked-up. HPLC (1:8 EtOAc/hexane) gave 4.2 g (87%) of 5-cyano-6-methoxy-2-methylthioquinoline as a light yellow solid, (M+) 230(100).

Step 5a

A solution of 5-cyano-6-methoxy-2-methylthioquinoline (3.2 g, 14 mmol) in toluene (30 mL) was treated with a 1.5 M solution of DIBAL in toluene (14 mL, 21 mmol). The mixture was heated to 30° C. for 14 hours. The mixture was cooled to 0° C., quenched with saturated aqueous NaCl, and extracted with EtOAc (2×). The combined organic layer was worked-up. HPLC (1:8 EtOAc/hexane) gave 1.4 g (43%) of 6-methoxy-2-methylthioquinoline-5-carboxaldehyde as a light yellow solid, (M+) 233(100).

A solution of 4-fluorobromobenzene (0.15 g, 0.86 mmol) in THF (5 mL) was treated with a 2.5 M solution of n-BuLi in hexane (0.36 mL, 0.90 mmol) at −78° C. After 20 min., compound 6-methoxy-2-methylthioquinoline-5-carboxaldehyde (0.20 g, 0.86 mmol)in THF (5 mL) was added. After an additional 30 min., the mixture was allowed to warm to ambient temperature for 5 h. The reaction was quenched with $H_2O$ and extracted with EtOAc. The organic layer was worked-up. HPLC (1:8 EtOAc/hexane) gave 0.19 g (67%) of 5-(4-fluorophenylhydroxymethano)-6-methoxy-2-methylthioquinoline, as an oil, (M+) 329(100).

Oxidation of 5-(4-fluorophenylhydroxymethano)-6-methoxy-2-methylthioquinoline with one equivalent of OXONE™ following steps 4 and 5 from Example 2 yielded:
1-(4-Fluoro-phenyl)-1-(2-methanesulfinyl-6-methoxy-quinolin-5-yl)-methanone 211 ([M+H]+) 344.

Replacement in step 5a of fluorobromobenzene with the following bromobenzenes and oxidation with one equivalent of OXONE™ gives the following compounds of Formula I:
4-chlorobromobenzene gives 1-(4-chloro-phenyl)-1-(2-methanesulfinyl-6-methoxy-quinolin-5-yl)-methanone 212 ([M+H]+) 360;
4-ethoxybromobenzene gives 1-(4-ethoxy-phenyl)-1-(2-methanesulfinyl-6-methoxy-quinolin-5-yl)-methanone, 213 ([M+H]+) 370; and
3-chloro-2-fluoro-6-methoxybenzene gives 1-(3-chloro-2-fluoro-6-methoxy-phenyl)-1-(2-methanesulfinyl-6-methoxy-quinolin-5-yl)-methanone, 214 ([M+H]+)=408.

Oxidation of 5-(4-fluorophenylhydroxymethano)-6-methoxy-2-methylthioquinoline with two equivalents of OXONE™ following steps 4 and 5 from Example 2 yielded:
1-(4-fluoro-phenyl)-1-(2-methanesulfonyl-6-methoxy-quinolin-5-yl)-methanone, 203. ([M+H]+) 360.

Similarly, replacement in step 5a of fluorobromobenzene with the following bromobenzenes and oxidation with two equivalents of OXONE™ give the following compounds of Formula I:
2-fluorobromobenzene gives 1-(2-fluoro-phenyl)-1-(2-methanesulfonyl-6-methoxy-quinolin-5-yl)-methanone, 204 ([M+H]+)=360;
2,4-Difluorobromobenzene gives 1-(2,4-difluoro-phenyl)-1-(2-methanesulfonyl-6-methoxy-quinolin-5-yl)-methanone, 205 ([M+H]+)=378;
4-Ethoxybromobenzene gives 1-(4-ethoxy-phenyl)-1-(2-methanesulfonyl-6-methoxy-quinolin-5-yl)-methanone, 206 ([M+H]+)=386; and
4-Chlorobromobenzene gives 1-(4-chloro-phenyl)-1-(2-methanesulfonyl-6-methoxy-quinolin-5-yl)-methanone, 207 ([M+H]+)=376.

Example 3

5-(2,4-Difluoro-benzenesulfinyl)-2-methanesulfonyl-6-methoxy-quinoline 301

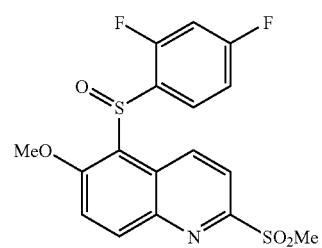

5-(2,4-Difluoro-phenylsulfanyl)-2-methanesulfonyl-6-methoxy-quinoline 101 (230 mg) was dissolved in 9 mL (1:1:1 MeOH/THF/$H_2O$) and was treated with 1 gram of OXONE™. After 3 hours the mixture was partitioned between $CH_2Cl_2$ and water. The product was purified by chromatography (10% MeOH/$CH_2Cl_2$) to afford 110 mg of 5-(2,4-difluoro-benzenesulfinyl)-2-methanesulfonyl-6-methoxy-quinoline 301; ([M+H]+)=398.

Example 4

5-(4-Fluoro-phenylsulfanyl)-2-methanesulfonyl-quinolin-6-ol 401

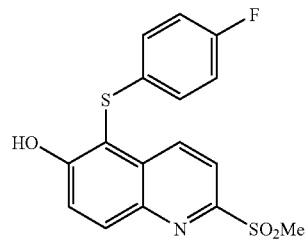

5-(4-Fluoro-phenylsulfanyl)-2-methanesulfonyl-6-methoxy-quinoline 102 (1 g) was dissolved in 5 mL DMF and treated with 500 mg LiCl and refluxed overnight. This mixture was partitioned between dilute HCl and EtOAc. The product was purified by chromatography (1:1 EtOAc/hexane) to provide 5-(4-fluoro-phenylsulfanyl)-2-methanesulfonyl-quinolin-6-ol; 401 (800 mg); ([M+H]⁺)=350.

Example 5

2-Methanesulfonyl-6-trifluoromethanesulfonoxy-5-(4-fluorophenyl)sulfanyl-quinoline 501

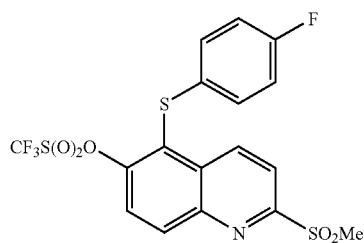

5-(4-Fluoro-phenylsulfanyl)-2-methanesulfonyl-quinolin-6-ol 401 (800 mg) was dissolved in 20 mL CH$_2$Cl$_2$ containing 1 mL triethylamine (NEt$_3$) and was cooled to ice-bath temperature. Trifluoromethanesulfonic anhydride (0.5 mL) was added. After 1 hour the mixture was partitioned between CH$_2$Cl$_2$ and aqueous NaHCO$_3$. The product was purified by chromatography (3:1 hexanes/EtOAc) to provide 2-methanesulfonyl-6-trifluoromethanesulfonoxy-5-(4-fluorophenyl)sulfanyl-quinoline 501 (1 g); ([M+H]⁺)=482.

Example 6

5-(2,4-Difluoro-benzyl)-2-methanesulfonyl-6-methoxy-quinoline 601

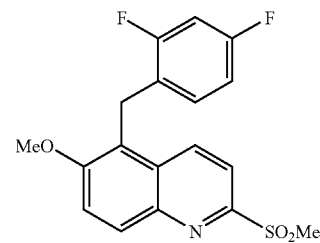

To the mixture of 3 g (9.5 mmol) 2-methylsulfone-5-bromo-6-methoxyquinoline and 1 g of tetrakis(triphenylphosphine)palladium (0) in pressure tube under nitrogen was added 95 mL of 0.5M solution of 2,4-difluorobenzylzinc bromide in THF. The reaction mixture in a pressure tube was stirred at 65° C. for 12 hours.

The reaction mixture was partitioned between water and methylene chloride, the organic phase was washed three times with water, dried over MgSO$_4$, and the solvent was removed under vacuum.

The resulting yellow crystalline material was triturated with ether to yield 2.8 g of 5-(2,4-difluoro-benzyl)-2-methanesulfonyl-6-methoxy-quinoline 601 ([M+H]⁺)=364.

Similarly, following the procedure described above, but replacing 2,4-difluorobenzylzinc bromide with other appropriate substituted benzylzinc bromides the additional compounds of Formula (Ih) wherein A is CH$_2$, were prepared:

4-fluorobenzyl zinc gives 5-(4-fluoro-benzyl)-2-methanesulfonyl-6-methoxy-quinoline; 602, ([M+H]⁺)=346;
2-fluorobenzyl zinc gives 5-(2-fluoro-benzyl)-2-methanesulfonyl-6-methoxy-quinoline; 603, ([M+H]⁺)=346;
4-ethoxybenzyl zinc gives 5-(4-ethoxy-benzyl)-2-methanesulfonyl-6-methoxy-quinoline; 604, ([M+H]⁺)=372;
4-methylbenzyl zinc gives 2-methanesulfonyl-6-methoxy-5-(4-methyl-benzyl)-quinoline; 605, ([M+H]⁺)=342;
4-methoxybenzyl zinc gives 2-methanesulfonyl-6-methoxy-5-(4-methoxy-benzyl)-quinoline; 606, ([M+H]⁺)=358; and
4-chlorobenzyl zinc gives 5-(4-chloro-benzyl)-2-methanesulfonyl-6-methoxy-quinoline; 607, ([M+H]⁺)=362.

Alternatively, (2,4-difluoro-benzyl)-2-methanesulfonyl-6-methoxy-quinoline 601 (363 mg) in 8 mL DMF was treated with 10 mmoles NaSMe, and stirred 30 min. It was partitioned between water and ether. The organic phase was evaporated to yield 5-(2,4-difluoro-benzyl)-6-methoxy-2-methylsulfanyl-quinoline, 608 ([M+H]⁺)=332. The resulting sulfide was dissolved in 10 mL 1:1 MeOH/THF and 0.5 mmole OXONE™ in 2 mL water was added. After 3 hours the solution was poured into water and extracted with CH$_2$Cl$_2$. The product 5-(2,4-difluoro-benzyl)-2-methanesulfinyl-6-methoxy-quinoline 609 was purified by PTLC on silica gel (1:1 hexane/EtOAc) to obtain 255 mg product ([M+H]⁺)=348.

Example 7

5-(2,4-Difluoro-phenoxy)-2-methanesulfonyl-6-methoxy-quinoline 701

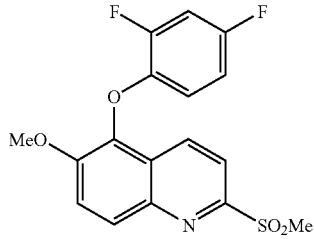

Step 1

2,4,-Difluorophenol (3.7 g, 28.6 mmol) was added to a solution of KOH (1.6 g, 28.6 mmol) in 40 mL of 2-ethoxyethanol, stirred for 10 min. at room temperature under N$_2$, followed by addition of 5-bromo-6-methoxy-8-nitroquinoline. The mixture was refluxed for 12 hours, stirred at room temperature for 6 hours and kept in the refrigerator overnight. The solvent was removed under vacuum; the residue was purified using a Biotage system, eluting with 20% EtOAc/Hexane. The product was crystallized from ethanol to yield 1.6 g (22.2%) of yellow crystals of 5-(2,4-difluorophenoxy)-6-methoxy-8-nitro-quinoline.

Step 2

To a solution of 5-(2,4-difluoro-phenoxy)-6-methoxy-8-nitro-quinoline (1.36 g, 4.1 mmol) in 30 mL of THF was added an aqueous solution of sodium hypophosphite (2.7 g, 31 mmol in 10 mL H$_2$O). The reaction mixture was degassed under N$_2$, treated with Pd/C (~1 g), and stirred at room temperature under N$_2$ for 1 hour. The reaction mixture was filtered through Celite®, and washed with 1N NaOH solution followed by water. The organic layer was dried over MgSO₄, and the solvent removed to give 0.9 g (75%) of 5-(2,4-difluoro-phenoxy)-6-methoxy-quinolin-8-ylamine.

Step 3

A solution of 2.4 mL HCl in 24 mL H₂O was heated to the boiling point and poured into 2.4 g (0.008 mol) of 5-(2,4-difluoro-phenoxy)-6-methoxy-quinolin-8-ylamine, then stirred while hot to dissolve as much solid as possible. The solution was cooled in an ice-salt mixture. When the temperature reached 15° C., 2.5 mL of conc. HCl were added to the reaction mixture. At 10° C. a solution of NaNO₂ (1.1 g, 0.016 mol in 2 mL of water) was added dropwise during 10 min. The reaction mixture was stirred at 5–10° C. for 30 min., treated with ice-cold 30% H₃PO₄, and cooled at 0° C. overnight. After stirring for an additional 8 hours,at room temperature, the reaction mixture was neutralized with 1N NaOH, extracted with CH₂Cl₂, and the organic layer was dried (MgSO₄). Solvent removal, followed by HPLC, eluting with 10–20% EtOAc/Hexane gave 1.5 g (66%) of 5-(2,4-difluoro-phenoxy)-6-methoxy-quinoline, which crystallized at room temperature.

Step 4

The solution of 5-(2,4-difluoro-phenoxy)-6-methoxy-quinoline in glacial acetic acid containing 4 ml hydrogen peroxide was stirred at 80–85° C. for 18 hours. After cooling the reaction mixture was neutralized with aqueous ammonia, and the resultant precipitate was filtered and washed with water. The aqueous layer was extracted with dichloromethane, and the organic layer was dried (MgSO₄). Evaporation gave 1.3 g ( 68%) of 5-(2,4-difluoro-phenoxy)-6-methoxy-quinoline N-oxide as a beige crystalline material.

Step 5

5-(2,4-Difluoro-phenoxy)-6-methoxy-quinoline N-oxide (1.35 g, 4.5 mmol) was mixed with 5 mL of acetic anhydride and stirred at 75° C. for 22 hours. The reaction mixture was poured on ice, neutralized with aqueous ammonia, and the resultant precipitate was filtered and washed with water. The aqueous layer was extracted with dichloromethane and the organic extract was dried over MgSO₄. The solvent was removed under vacuum. The dry residue, combined with the filtered precipitate, was dissolved in a minimum amount of CH₂Cl₂ and purified using a Biotage system, eluting with 10–30% EtOAc/hexane to give 0.3 g (22.2%) of 5-(2,4-difluoro-phenoxy)-6-methoxy-1H-quinolin-2-one.

Step 6

A solution of 5-(2,4-difluoro-phenoxy)-6-methoxy-1H-quinolin-2-one derivative (0.3 g) in 10 mL of POCl₃ was refluxed for 1.5 hours. POCl₃ was removed under vacuum, the residue was stirred with saturated aqueous sodium bicarbonate solution, the product was extracted with methylene chloride, and the organic layer was dried (MgSO₄). Solvent removal gave 0.28 g (87.5%) of 2-chloro-5-(2,4-difluoro-phenoxy)-6-methoxy-quinoline as pure white crystals.

Step 7

A solution of 2-chloro-5-(2,4-difluoro-phenoxy)-6-methoxy-quinoline (0.28 g) in 10 mL of DMF was treated with 1 equivalent of NaSCH₃ and stirred for 30 min. at room temperature. The reaction mixture was partitioned between water and methylene chloride, the organic layer was dried over MgSO₄, the solvent was evaporated in vacuum, and the remaining DMF was removed under vacuum to yield 0.25 g of 5-(2,4-difluoro-phenoxy)-6-methoxy-2-methylsulfanyl-quinoline 712, as white crystals ([M+H]+)=334.

Step 8

A solution of 0.25 g of 5-(2,4-difluoro-phenoxy)-6-methoxy-2-methylsulfanyl-quinoline in 10 mL of methanol was treated with aqueous OXONE™ solution (1.3 g in 5 mL H2O) and stirred for 2 hours at room temperature. The reaction mixture was partitioned between water and dichloromethane, the organic layer was dried (MgSO₄), and the solvent was removed under vacuum. The solid residue was dissolved in a minimum amount of dichloromethane and washed through a silica gel plug to remove the baseline impurities. Elution with 30% EtOAc/hexane yielded 0.11 g (38%) of 5-(2,4-difluoro-phenoxy)-2-methanesulfonyl-6-methoxy-quinoline 701 ([M+H]⁺)=366, as white crystals.

Similarly, following the procedure described above, but replacing 2,4,-difluorophenol with other appropriate substituted phenols the additional compounds of Formula (Ih) wherein A is CH₂, were prepared:

2-Fluoro-4-methanesulfonyl-phenol gives 5-(2-fluoro-4-methanesulfonyl-phenoxy)-2-methanesulfonyl-6-methoxy-quinoline, 702 ([M+H]⁺)=426;

4-Fluorophenol gives 5-(4-fluoro-phenoxy)-2-methanesulfonyl-6-methoxy-quinoline, 703 ([M+H]⁺)=348;

2-Chloro-4-methoxy-phenol gives 5-(2-chloro-4-methoxy-phenoxy)-2-methanesulfonyl-6-methoxy-quinoline, 704 ([M+H]⁺)=394;

4-Ethoxy-phenol gives 5-(4-ethoxy-phenoxy)-2-methanesulfonyl-6-methoxy-quinoline, 705 ([M+H]⁺)=374;

Phenol gives 2-methanesulfonyl-6-methoxy-5-phenoxy-quinoline, 706 ([M+H]⁺)=330;

2-Fluoro-phenol gives 5-(2-fluoro-phenoxy)-2-methanesulfonyl-6-methoxy-quinoline, 707 ([M+H]⁺)=348;

2,6-Difluoro-phenol gives 5-(2,6-difluoro-phenoxy)-2-methanesulfonyl-6-methoxy-quinoline, 708 ([M+H]⁺)=366, and 2-Fluoro-6-methanesulfonyl-phenol gives 5-(2-fluoro-6-methanesulfonyl-phenoxy)-2-methanesulfonyl-6-methoxy-quinoline, 709 ([M+H]⁺)=426.

Alternatively, following the procedure described above, but using one an equivalent of OXONE™ in step 8, the additional compounds of Formula (I) wherein A is —O—, and R3 is —SOR¹² were prepared:

5-(2,4-Difluoro-phenoxy)-2-methanesulfinyl-6-methoxy-quinoline, 710 ([M+H]⁺)=349; and 5-(4-Fluoro-phenoxy)-2-methanesulfinyl-6-methoxy-quinoline 711 ([M+H]⁺)=332

Example 8

The following are representative pharmaceutical formulations containing a compound of Formula I.

Tablet Formulation

The following ingredients are mixed intimately and pressed into single scored tablets.

| Ingredient | Quantity per tablet, mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per tablet, mg |
|---|---|
| compound of this invention | 200 |
| lactose, spray-dried | 148 |
| magnesium stearate | 2 |

Suspension Formulation

The following ingredients are mixed to form a suspension for oral administration.

| Ingredient | Amount |
|---|---|
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Injectable Formulation

The following ingredients are mixed to form an injectable formulation.

| Ingredient | Amount |
|---|---|
| compound of this invention | 0.4 mg |
| sodium acetate buffer solution, 0.4M | 2.0 mL |
| HCl (1N) or NaOH (1N) | q.s. to suitable pH |
| water (distilled, sterile) | q.s.to 20 mL |

Example 9

Inhibition of COX I and COX II In Vitro

The COX I and COX II inhibitory activity of compounds of this invention in vitro was determined using partially purified COX I and COX II enzymes, prepared as described in J. Barnett et. al., *Biochim. Biophys. Acta,* 1209, 130–139 (1994).

COX I and COX II samples were diluted with Tris-HCl buffer (50 mM Tris-HCl, pH 7.9) containing 2 mM EDTA and 10% glycerol and reconstituted by incubating first with 2 mM phenol for 5 minutes and then with 1 micromolar hematin for an additional 5 minutes. 125 µl of the reconstituted COX I or COX II enzyme were preincubated for 10 minutes at room temperature in a shaking water bath with the compounds of the invention dissolved in 2–15 µl of DMSO or the carrier vehicles (control samples). The enzyme reaction was initiated by adding 25 µl of 1-[14 C]arachidonic acid (80,000–100,000 cpm/tube; 20 micromolar final concentration) and the reaction was allowed to continue for an additional 45 seconds. The reaction was terminated by adding 100 µl of 2N HCl and 750 µl water. An aliquot (950 µl) of the reaction mixture was loaded onto a 1 mL $C_{18}$ Sep-Pak column (J. T. Baker, Phillipsburg, N.J.) which had been previously washed with 2–3 mL methanol and equilibrated with 5–6 mL distilled water. Oxygenated products were quantitatively eluted with 3 mL of acetonitrile/water/acetic acid (50:50:0.1, v/v) and the radioactivity in the eluate determined in a scintillation counter. Compounds of this invention were active in this assay for COX II.

The COX inhibitory activities (expressed as $IC_{50}$, the concentration causing 50% inhibition of the COX enzyme being assayed) of some exemplary compounds of the invention were:

| CPD # | COX I $IC_{50}$, µM | COX II $IC_{50}$, µM |
|---|---|---|
| 101 | >40 | <0.20 |
| 104 | >40 | <0.20 |
| 105 | >40 | <0.20 |
| 106 | >40 | <0.30 |
| 107 | >40 | <0.30 |

Example 10

Anti-Inflammatory Activity

The anti-inflammatory activity of compounds of this invention was determined by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" *Proc. Soc. Exp. Biol. Med.* 111, 544–547, (1962). This assay has been used as a primary in vivo screen for anti-inflammatory activity of most NSAIDs, and is considered predictive of human efficacy. Briefly, test materials were administered orally to female rats in a volume of 1 mL prepared as solutions or suspensions in an aqueous vehicle containing 0.9% sodium chloride, 0.5% sodium carboxymethyl-cellulose, 0.4% polysorbate 80, 0.9% benzyl alcohol and 97.3% distilled water. Control rats received vehicle alone. After 1 h 0.05 mL of a 0.5% solution of Carrageenan (Type IV Lambda, Sigma Chemical Co.) in 0.9% saline was injected into the subplantar region of the right hind paw. Three hours later the rats were euthanized in a carbon dioxide atmosphere; hind paws were removed by severing at the tatso-crural joint; and the left and right paws were weighed. The increase in weight of the right paw over the left paw was obtained for each animal and the mean increases were calculated for each group. The anti-inflammatory activity of the test materials is expressed as the percent inhibition of the increase in hind paw weight of the test group relative to the vehicle dosed control group.

Compounds of this invention were active in this assay.

Example 11

Inhibition of Eicosanoid Synthesis In Vivo

The activity of compounds of this invention in inhibiting in vivo eicosanoid (prostaglandin $E_2$) synthesis in inflamed tissues was determined by the carrageenan-induced inflammation (air-pouch model) in rats, using a modification of the method described in Futaki, M., et al., "Selective Inhibition of NS-398 on prostanoid production in inflamed tissue in rat Carrageenan Air-pouch Inflammation" *J. Pharm. Pharmacol.* 45, 753–755, (1993) and Masferrer, J. L., et al.; "Selective Inhibition of inducible cyclooxygenase 2 in vivo is Antiinflammatory and Nonulcerogenic" *Proc. Natl. Acad. Sci. USA.* 91, 3228–3232, (1994). In this assay, an air-pouch is created in the rat and the $PGE_2$ levels in the air-pouch exudate are measured by enzyme immunoassay. Briefly, male rats were anesthetized using a 60:40 $CO_2$:$O_2$ mixture and subsequently injected subcutaneously with 20 mL of sterilized air, under aseptic conditions, in the proximal area of the dorsum. This injection of sterile air causes the creation of a subcutaneous "air pouch". The next day, a further 10 mL of sterile air was injected into the previously formed pouch using the same technique. The test materials were administered orally in a volume of 1 mL/100 g body weight as solutions or suspensions in an aqueous vehicle containing 0.9% sodium chloride, 0.5% sodium carboxymethyl-cellulose, 0.4% polysorbate 80, 0.9% benzyl alcohol and 97.3% water. Control rats received vehicle alone. After 30 minutes, 5 mL of a 0.5% solution of carrageenan (Sigma, Lambda Type IV) was injected into the air pouch. The rats were euthanized 3 or 6 h after the compound administration. 10 mL of a solution containing 10 µg/l of indomethacin and 5.4 mM EDTA in 0.9% sterile saline was injected into the air pouch; the air pouch was cut open; and the exudate was harvested. The total exudate volume was recorded, and the samples were analyzed for $PGE_2$ and 6-keto $PGF_1$ by ELISA (Titerzyme®, PerSeptive Diagnostics, Boston, Mass.) and $TxB_2$ by radioimmuno assay (New England Nuclear Research, Boston Mass., Catalog No. NEK-037), according to the manufacturer's directions.

The mean concentrations of $PGE_2$ were calculated for each group. The anti-inflammatory activity of test materials is expressed as the percent inhibition of $PGE_2$ formation in the test group relative to the control group.

Compounds of this invention were active in this assay.

Example 12

Analgesic Activity

The analgesic activity of the compounds of this invention may be determined by using a modification of the method described in Randall, L. O., and Selitto, J. J., "A Method for Measurement of Analgesic Activity on Inflamed Tissue", *Arch. Int. Pharmacodyn.*, CXI, 4, 409, (1957) and Gans, et. al., "Anti-Inflammatory and Safety Profile of DuP 697, a Novel Orally Effective Prostaglandin Synthesis Inhibitor", *J. Pharmacol. Exp. Ther.*, 254, No. 1, 180, (1990). In this assay, the male Sprague Dawley rats were injected with 0.1 mL of 20% brewer's yeast in deionized water (Sigma, St. Louis) in the subplantar region of the left hind foot. After 2 h, the test materials were administered orally in a volume of 1 mL/100 g body weight as solutions or suspensions in an aqueous vehicle containing 0.9% sodium chloride, 0.5% sodium carboxymethyl-cellulose, 0.4% polysorbate 80, 0.9% benzyl alcohol and 97.3% water. Control rats received vehicle alone. After 1 h, the hindpaw was placed on the platform of a Basile Analgesy-Meter (Ugo Biological Research Apparatus, Italy, Model #7200) and mechanical force was applied to the dorsum of the rat's hindpaw. Compounds of the invention were active in this assay.

The analgesic activity of compounds of this invention may also be determined by using an adjuvant-induced arthritis pain model in the rat, where pain is assessed by the animal's vocal response to the squeezing or flexing of an inflamed ankle joint, as described in Winter C. A. and Nuss, G. W., "Treatment of Adjuvant Arthritis in rats with Antiinflammatory Drugs", *Arthritis Rheum.*, 9, 394–403, (1966) and Winter, C. A., Kling P. J., Tocco, D. J., and Tanabe, K., "Analgesic activity of Diflunisal [MK-647; 5-(2,4-Difluorophenyl)salicylic acid] in Rats with Hyperalgesia Induced by Freund's Adjuvant", *J. Pharmacol. Exp. Ther.*, 211, 678–685, (1979).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound selected from the group of compounds represented by Formula I:

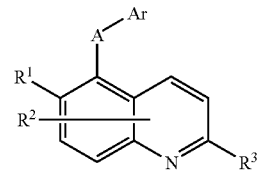

wherein:
A is a —$CH_2$—, —C(O)—, —O—, —S—, —S(O)—, or —$S(O)_2$—,
Ar is an optionally-substituted phenyl;
$R^1$ is cycloalkyl, haloalkyloxy, hydroxyalkyloxy, hydroxy, halo, or cyano;
$R^2$ is hydrogen, alkyl, alkenyl, alkoxy, hydroxy, halo, or haloalkyl;
$R^3$ is —$SO_2R^{12}$, wherein,
$R^{12}$ is alkyl, hydroxyalkyl, alkoxyalkyl, aminoalkyl, mono or dialkylaminoalkyl, carboxyalkyl, or alkoxycarbonylalkyl; and
prodrugs, and pharmaceutically acceptable salts thereof.

2. A compound of claim 1 wherein A is —S—.

3. A compound of claim 2 wherein
$R^1$ is alkoxy, hydroxy, halogen or cyano;
$R^2$ is hydrogen or methyl; and
$R^3$ is $SO_0R^{12}$ where $R^{12}$ is alkyl.

4. A compound of claim 3 wherein Ar is unsubstituted phenyl.

5. A compound of claim 3 wherein Ar is 4-substituted phenyl or 2-substituted phenyl.

6. A compound of claim 3 wherein Ar is a disubstituted phenyl.

7. A compound of claim 3 wherein Ar is optionally substituted at one or more positions with a substitutent or substituents independently selected from the group consisting of fluoro, chloro, bromo, ethoxy, and methoxy.

8. A compound of claim 1 wherein A is —C(O)—.
9. A compound of claim 8 wherein
   $R^1$ is alkoxy, hydroxy, halogen or cyano;
   $R^2$ is hydrogen or methyl; and
   $R^3$ is $SO_0R^{12}$ where $R^{12}$ is alkyl.
10. A compound of claim 9 wherein Ar is unsubstituted phenyl.
11. A compound of claim 9 wherein Ar is 4-substituted phenyl, 2-substituted phenyl, or disubstituted phenyl.
12. A compound of claim 9 wherein Ar is optionally substituted at one or more positions with a substitutent or substituents independently selected from the group consisting of fluoro, chloro, bromo, ethoxy, and methoxy.
13. A compound of claim 1 wherein A is —CH$_2$—.
14. A compound of claim 13 wherein
   $R^1$ is alkoxy, hydroxy, halogen or cyano;
   $R^2$ is hydrogen or methyl; and
   $R^3$ is $SO_2R^{12}$ where $R^{12}$ is alkyl.
15. A compound of claim 14 wherein Ar is unsubstituted phenyl.
16. A compound of claim 14 wherein Ar is 4-substituted phenyl, 2-substituted phenyl or disubstituted phenyl.
17. A compound of claim 14 wherein Ar is optionally substituted at one or more positions with a substitutent or substituents independently selected from the group consisting of fluoro, chloro, bromo, ethoxy, and methoxy.
18. A compound of claim 1 wherein A is —O—.
19. A compound of claim 18 wherein
   $R^1$ is alkoxy, hydroxy, halogen or cyano;
   $R^2$ is hydrogen or methyl; and
   $R^3$ is $SO_2R^{12}$ where $R^{12}$ is alkyl.
20. A compound of claim 19 wherein Ar is unsubstituted phenyl.
21. A compound of claim 19 wherein Ar is 4-substituted phenyl or 2-substituted phenyl.
22. A compound of claim 19 wherein Ar is a disubstituted phenyl.
23. A compound of claim 19 wherein Ar is optionally substituted at one or more positions with a substitutent or substituents independently selected from the group consisting of fluoro, chloro, bromo, ethoxy, and methoxy.
24. A pharmaceutical composition comprising a therapeutically effective amount of a compound of claim 1 and a pharmaceutically acceptable excipient.
25. A method of treating inflammatory disease or pain in a mammal treatable by administration of a selective COX II inhibitor comprising administration to the mammal a therapeutically effective amount of a compound of claim 1.
26. The method of claim 25, wherein the inflammatory disease or pain is selected from arthritis (rheumatoid arthritis and osteoarthritis), back pain, dental pain, pain and inflammation associated with sports injuries, sprains, strains, tendonitis, and ankylosing spondylitis.
27. The method of treatment of dysmenorrhoea or premature labor in a mammal comprising administration to the mammal a therapeutically effective amount of a compound of claim 1.
28. A process for preparing a compound selected from the group of compounds of claim 1, which comprises
   reacting a compound of general formula

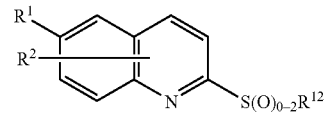

wherein $R^1$, $R^2$, and $R^{12}$ are as defined in claim 1,
with a compound of general formula ArSH, to provide a compound of Formula I:

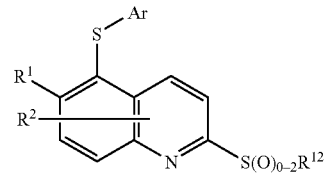

wherein Ar, $R^1$, $R^2$, and $R^{12}$ are as defined in claim 1.

29. A process for preparing a compound selected from the group of compounds of claim 1, which comprises
   reacting a compound of general Formula

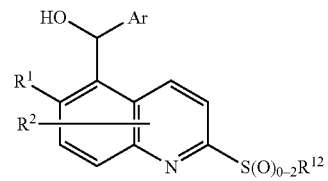

wherein $R^1$, $R^2$, and $R^{12}$, are as defined in claim 1,
with an oxidizing agent to provide a compound of Formula I:

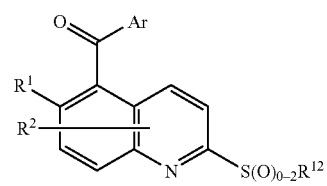

wherein Ar, $R^1$, $R^2$, and $R^{12}$ are as defined in claim 1.

30. A process for preparing a compound selected from the group of compounds of claim 1, which comprises
   reacting a compound of general formula

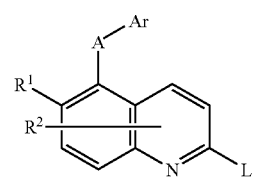

wherein A is —NR$^5$— or —O—, and L is a leaving group,
with a compound of general formula NaSR$^{12}$, followed by optional oxidation to provide a compound of Formula I:

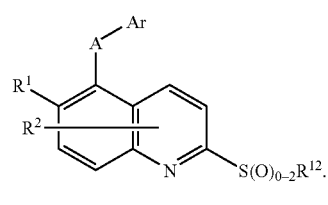

31. A process for preparing a compound selected from the group of compounds of claim 1, which comprises reacting a compound of general formula

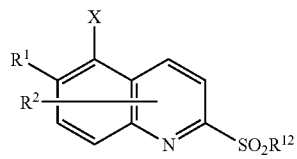

wherein X is a halogen, with an aralkyl anion compound to provide a compound of Formula I:

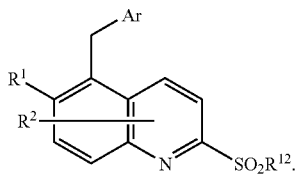

32. A compound having the formula:

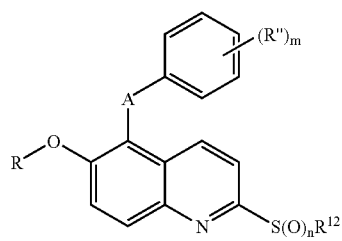

wherein:
 A is a —$CH_2$—, C(O)—, —O—, or —S—;
 R is hydrogen, alkyl, haloalkyl, or $SO_2R^{11}$ where $R^{11}$ is selected from alkyl, cycloalkyl, and haloalkyl;
 $R^{12}$ is alkyl, hydroxyalkyl, alkoxyalkyl, aminoalkyl, mono or dialkylaminoalkyl, carboxyalkyl, or alkoxycarbonylalkyl;
 R" is at each occurrence independently selected from halo, cyano, nitro, alkyl, hydroxy, alkoxy, amino, acylamino, alkylamino, dialkylamino, haloalkyl, haloalkoxy, and heteroalkyl;
 m is 0, 1, 2, 3, or 4; and
 n is 1, 2 or 3; and
prodrugs, individual isomers, mixtures of isomers, and pharmaceutically acceptable salts thereof.

33. A compound according to claim 32, or a pharmaceutically-acceptable salt or prodrug thereof in which:
 A is S;
 R is $CH_3$;
 R" is at each occurrence independently selected from halo, cyano, $C_{1-4}$ alkyl, hydroxy, methoxy, ethoxy, trifluoromethyl, or trifluoromethoxy; and
 m is 0, 1, or 2.

* * * * *